US010288623B2

(12) United States Patent
Todd et al.

(10) Patent No.: US 10,288,623 B2
(45) Date of Patent: May 14, 2019

(54) METHODS FOR DIAGNOSING, STAGING, PREDICTING RISK FOR DEVELOPING AND IDENTIFYING TREATMENT RESPONDERS FOR RHEUMATOID ARTHRITIS

(71) Applicant: Singulex, Inc., Alameda, CA (US)

(72) Inventors: John Allan Todd, Lafayette, CA (US); Quynh Anh Thuc Lu, Mountain View, CA (US); Sara Jane Le, Berkeley, CA (US)

(73) Assignee: SINGULEX, INC., Alameda, CA (US)

( * ) Notice: Subject to any disclaimer, the term of this patent is extended or adjusted under 35 U.S.C. 154(b) by 0 days.

(21) Appl. No.: 14/476,820

(22) Filed: Sep. 4, 2014

(65) Prior Publication Data

US 2015/0119275 A1   Apr. 30, 2015

Related U.S. Application Data

(63) Continuation of application No. 13/102,683, filed on May 6, 2011, now abandoned.

(60) Provisional application No. 61/332,081, filed on May 6, 2010, provisional application No. 61/428,500, filed on Dec. 30, 2010, provisional application No. 61/444,702, filed on Feb. 19, 2011.

(51) Int. Cl.
  *G01N 33/68*   (2006.01)
  *G01N 33/564*   (2006.01)

(52) U.S. Cl.
  CPC ....... *G01N 33/6869* (2013.01); *G01N 33/564* (2013.01); *G01N 33/6893* (2013.01); *G01N 2333/34* (2013.01); *G01N 2333/54* (2013.01); *G01N 2800/065* (2013.01); *G01N 2800/102* (2013.01); *G01N 2800/122* (2013.01); *G01N 2800/205* (2013.01); *G01N 2800/50* (2013.01); *G01N 2800/52* (2013.01); *G01N 2800/56* (2013.01)

(58) Field of Classification Search
  None
  See application file for complete search history.

(56) References Cited

U.S. PATENT DOCUMENTS

| | | |
|---|---|---|
| 4,071,298 A | 1/1978 | Falconer |
| 4,172,227 A | 10/1979 | Tryer et al. |
| 4,243,318 A | 1/1981 | Stohr |
| 4,251,733 A | 2/1981 | Hirleman, Jr. |
| 4,452,773 A | 6/1984 | Molday |
| 4,521,733 A | 6/1985 | Bottomley |
| 4,768,879 A | 9/1988 | McLachlan et al. |
| 4,770,183 A | 9/1988 | Groaman et al. |
| 4,793,705 A | 12/1988 | Shera |
| 4,927,265 A | 5/1990 | Brownlee |
| 4,972,265 A | 11/1990 | Tanaka et al. |
| 4,979,824 A | 12/1990 | Mathies et al. |
| 5,002,389 A | 3/1991 | Benser |
| 5,041,733 A | 8/1991 | Noguchi et al. |
| 5,094,594 A | 3/1992 | Brennan |
| 5,108,179 A | 4/1992 | Myers |
| 5,138,170 A | 8/1992 | Noguichi et al. |
| 5,209,834 A | 5/1993 | Shera |
| 5,230,997 A | 7/1993 | Frenkel |
| 5,269,937 A | 12/1993 | Dollinger et al. |
| 5,274,240 A | 12/1993 | Mathies et al. |
| 5,290,834 A | 3/1994 | Kadota et al. |
| 5,385,707 A | 1/1995 | Miltenyi et al. |
| 5,480,614 A | 1/1996 | Kamahori |
| 5,540,494 A | 7/1996 | Purvis, Jr. et al. |
| 5,543,838 A | 8/1996 | Hosier et al. |
| 5,547,849 A | 8/1996 | Bear et al. |
| 5,571,410 A | 11/1996 | Swedberg et al. |
| 5,603,351 A | 2/1997 | Cherukuri et al. |
| 5,605,662 A | 2/1997 | Heller et al. |
| 5,633,503 A | 5/1997 | Kosaka |
| 5,653,859 A | 5/1997 | Parton et al. |
| 5,645,702 A | 7/1997 | Witt et al. |
| 5,653,939 A | 8/1997 | Hollis et al. |
| 5,658,413 A | 8/1997 | Kaltenbach et al. |
| 5,681,751 A | 10/1997 | Begg et al. |
| 5,682,038 A | 10/1997 | Hoffman |
| 5,716,825 A | 2/1998 | Hancock et al. |
| 5,730,187 A | 3/1998 | Howtiz et al. |
| 5,746,901 A | 5/1998 | Balch et al. |
| 5,755,942 A | 5/1998 | Zanzucchi et al. |
| 5,770,029 A | 6/1998 | Nelson et al. |
| 5,793,485 A | 8/1998 | Gourley |
| 5,795,158 A | 8/1998 | Warinner |

(Continued)

FOREIGN PATENT DOCUMENTS

| | | |
|---|---|---|
| DE | 3720844 | 1/1989 |
| WO | 1990/10876 | 9/1990 |

(Continued)

OTHER PUBLICATIONS

Wright et al, The Journal of Biological Chemistry vol. 282, No. 18, pp. 13447-13455.*
Miossec et al, Microbes and Infection, 2009; vol. 11, pp. 625-630.*
Erenna® IL-17A Immunoassay Kit data sheet; 2006.*
Erenna® IL-β Immunoassay Kit; 2006.*
Schultze et al, Toxicologic Pathology, 2008, vol. 36, pp. 777-782.*
Gilmore et al; Diabetes, Jun. 2008); vol. 57, No. Suppl. 1, pp. A413.*
Todd et al, Drug Discovery, 2008, pp. 51-57.*
Leger et al, Journal of Immunological Methods, 2009, vol. 350, pp. 161-170.*
Apple, Clinical Biochemistry., May 2010, vol. 43, pp. 1034-1036.*
Guide to Labeling Antibodies with Alexa Fluor Dyes, 2004, pp. 24-28.

(Continued)

*Primary Examiner* — Bridget E Bunner
*Assistant Examiner* — Fozia Hamud
(74) *Attorney, Agent, or Firm* — McDonnell Boehnen Hulbert & Berghoff LLP

(57) ABSTRACT

Disclosed are methods for diagnosing, staging, and predicting risk for developing rheumatoid arthritis and other inflammatory diseases, and methods for identifying treatment responders and non-responders.

23 Claims, 11 Drawing Sheets

(56) References Cited

U.S. PATENT DOCUMENTS

| | | |
|---|---|---|
| 5,795,758 A | 8/1998 | Gentry et al. |
| 5,798,222 A | 8/1998 | Goix |
| 5,807,677 A | 9/1998 | Eigen et al. |
| 5,858,195 A | 1/1999 | Ramsey |
| 5,863,801 A | 1/1999 | Southgate et al. |
| 5,925,533 A | 7/1999 | Doth et al. |
| 5,949,532 A | 9/1999 | Schrof et al. |
| 5,955,028 A | 9/1999 | Chow |
| 5,989,402 A | 11/1999 | Chow et al. |
| 5,999,250 A | 12/1999 | Hairston et al. |
| 6,033,628 A | 3/2000 | Kaltenbach et al. |
| 6,041,515 A | 3/2000 | Ally et al. |
| 6,049,380 A | 4/2000 | Goodwin et al. |
| 6,071,478 A | 6/2000 | Chow |
| 6,114,180 A | 9/2000 | Doth et al. |
| 6,130,101 A | 10/2000 | Maitino et al. |
| 6,132,580 A | 10/2000 | Mathies et al. |
| 6,140,048 A | 10/2000 | Muller et al. |
| 6,143,152 A | 11/2000 | Simpson et al. |
| 6,177,277 B1 | 1/2001 | Soini |
| 6,208,815 B1 | 3/2001 | Seidel et al. |
| 6,211,955 B1 | 4/2001 | Basiji et al. |
| 6,242,266 B1 | 6/2001 | Schleifer et al. |
| 6,249,341 B1 | 6/2001 | Basiji et al. |
| 6,280,960 B1 | 8/2001 | Carr |
| 6,309,886 B1 | 10/2001 | Ambrose et al. |
| 6,338,746 B1 | 1/2002 | Detrick et al. |
| 6,355,420 B1 | 3/2002 | Chan |
| 6,361,371 B2 | 3/2002 | Mathies et al. |
| 6,361,671 B1 | 3/2002 | Mathies et al. |
| 6,372,185 B1 | 4/2002 | Shumate et al. |
| 6,386,219 B1 | 5/2002 | Barth et al. |
| 6,388,746 B1 | 5/2002 | Eriksson et al. |
| 6,394,305 B1 | 5/2002 | Sydlosky et al. |
| 6,403,338 B1 | 6/2002 | Knapp et al. |
| 6,403,947 B1 | 6/2002 | Hoyt et al. |
| 6,473,176 B2 | 11/2002 | Basiji et al. |
| 6,482,648 B2 | 11/2002 | Doth et al. |
| 6,495,104 B1 | 12/2002 | Unno et al. |
| 6,506,609 B1 | 1/2003 | Wada et al. |
| 6,532,067 B1 | 3/2003 | Chang et al. |
| 6,533,553 B2 | 3/2003 | Caren |
| 6,537,437 B1 | 3/2003 | Galambos et al. |
| 6,554,744 B2 | 4/2003 | Schmidt |
| 6,582,903 B1 | 6/2003 | Rigler et al. |
| 6,599,436 B1 | 7/2003 | Matzke et al. |
| 6,608,680 B2 | 8/2003 | Basiji et al. |
| 6,623,613 B1 | 9/2003 | Mathies et al. |
| 6,624,785 B2 | 9/2003 | Poliak et al. |
| 6,689,323 B2 | 2/2004 | Fisher et al. |
| 6,710,871 B1 | 3/2004 | Goix |
| 6,749,734 B1 | 6/2004 | Simpson et al. |
| 6,766,817 B2 | 7/2004 | da Silva |
| 6,783,992 B2 | 8/2004 | Robotti et al. |
| 6,802,342 B2 | 10/2004 | Fernandes et al. |
| 6,811,668 B1 | 11/2004 | Berndt et al. |
| 6,816,257 B2 | 11/2004 | Goix |
| 6,918,404 B2 | 7/2005 | Dias da Silva |
| 6,977,305 B2 | 12/2005 | Leung et al. |
| 6,991,907 B1 | 1/2006 | Buechler et al. |
| 7,066,586 B2 | 6/2006 | da Silva |
| 7,074,194 B2 | 7/2006 | Crosby |
| 7,572,640 B2 | 8/2009 | Goix et al. |
| 2002/0030812 A1 | 3/2002 | Ortyn et al. |
| 2002/0123059 A1 | 9/2002 | Ho |
| 2002/0167665 A1 | 11/2002 | Yeung et al. |
| 2003/0029995 A1 | 2/2003 | Mullins et al. |
| 2003/0078737 A1 | 4/2003 | Keys et al. |
| 2003/0109420 A1 | 6/2003 | Valkirs et al. |
| 2003/0124592 A1 | 7/2003 | Puskas |
| 2003/0125231 A1 | 7/2003 | Li et al. |
| 2003/0222007 A1 | 12/2003 | Gu et al. |
| 2004/0166514 A1 | 8/2004 | Puskas et al. |
| 2004/0214211 A1 | 10/2004 | Gilmanshin et al. |
| 2004/0219509 A1 | 11/2004 | Valkirs et al. |
| 2004/0219604 A1 | 11/2004 | Eriksson et al. |
| 2005/0064523 A1 | 3/2005 | Wu |
| 2005/0164205 A1 | 7/2005 | Puskas |
| 2005/0221408 A1 | 10/2005 | Nalefski et al. |
| 2005/0272054 A1 | 12/2005 | Cargill et al. |
| 2006/0003333 A1 | 1/2006 | Puskas |
| 2006/0004188 A1 | 1/2006 | Leung et al. |
| 2006/0078915 A1 | 4/2006 | Fuchs et al. |
| 2006/0078998 A1 | 4/2006 | Puskas et al. |
| 2006/0099638 A1 | 5/2006 | Leung et al. |
| 2006/0160209 A1 | 7/2006 | Larson et al. |
| 2006/0228747 A1 | 10/2006 | Fuchs et al. |
| 2007/0111316 A1 | 5/2007 | Shi et al. |
| 2007/0160576 A1 | 7/2007 | Arnott et al. |
| 2007/0196371 A1 | 8/2007 | Kuestner et al. |
| 2007/0249533 A1 | 10/2007 | Levin et al. |
| 2007/0259377 A1 | 11/2007 | Urdea et al. |
| 2008/0003685 A1 | 1/2008 | Goix et al. |
| 2008/0064113 A1 | 3/2008 | Goix et al. |
| 2008/0158543 A1 | 7/2008 | Puskas et al. |
| 2008/0161540 A1 | 7/2008 | Arnott et al. |
| 2008/0171352 A1 | 7/2008 | Goix et al. |
| 2008/0261242 A1 | 10/2008 | Goix et al. |
| 2009/0155271 A1 | 6/2009 | Levin et al. |
| 2009/0159812 A1 | 6/2009 | Livingston |
| 2009/0171590 A1 | 7/2009 | Puskas et al. |
| 2009/0197344 A1 | 8/2009 | Villard-Saussine et al. |
| 2010/0173321 A1 | 7/2010 | Hamm et al. |
| 2010/0255518 A1 | 10/2010 | Goix et al. |
| 2010/0329929 A1 | 12/2010 | Goix et al. |
| 2011/0111524 A1 | 5/2011 | Goix et al. |

FOREIGN PATENT DOCUMENTS

| | | |
|---|---|---|
| WO | 1999/026067 | 5/1999 |
| WO | 1999/40416 | 8/1999 |
| WO | 1999/54497 | 10/1999 |
| WO | 1999/55461 | 11/1999 |
| WO | 2004/059293 | 7/2004 |
| WO | 2005/089524 | 9/2005 |
| WO | 2006/036182 | 4/2006 |
| WO | 2008/048371 | 4/2008 |

OTHER PUBLICATIONS

Haab et al., "Single Molecule Florescence Burst Detection of DNA Fragments Separated by Capillary Electrophoresis", Anal Chem., 1995, pp. 3523-3260, vol. 67.

Haab et al., "Single-Molecule Detection of DNA Separations in Microfabricated Capillary Electrophoresis Chips Employing Focused Molecular Stream," Anal Chem., 1999, pp. 5137-5145, vol. 71.

Haughland, R.P., Molelcular Probes Handbook of Fluorescent Probes and Research Product, Ninth Edition, Molecular Probes, Inc.,2002, 12 pages.

Hirst et al., "Production of plasma selectively depleted in fibrinogen by affinity chromatography," Journal of Clinical Pathology, 1991, pp. 306-308, vol. 44.

Hubl et al., "Evaluation of the Architect Stat Troponin-I assay," Clinical Laboratory Publications, 2005, pp. 251-255, vol. 51.

Huse et al., "Application of a Filamentous Phag pVIII Fusion Protein System Suitable for Efficient Production, Screening and Mutageneis of F(ab) Antibody Fragments," J. Immunology, Dec. 15, 1992, pp. 3914-3920, vol. 149.

Kaiser et al.: "Capillary electrophoresis coupled to mass spectrometer for automated and robust polypeptide determination in body fluids for clinical use," Electrophoresis, 2004, pp. 2044-2055, vol. 25.

Katus et al., "Higher sensitivity troponin assyas: Quo vadis?" Eur Heart J., Jan. 2009, pp. 127-128, vol. 30, No. 2.

Keller et al., "Analytical Applications of Single-Molecule Detection," Analytical Chemistry, Jun. 1, 2002, pp. 317A-324A, vol. 74.

Kemp et al., "Biochemical markers of myocardial injury," British Journal of Anaesthesia, 2004, pp. 63-73, vol. 93.

Klee, George G., "Human Anti-Mouse Antibodies," Arch Pathol Lab Med., Jun. 2000, pp. 921-923. vol. 124.

(56) References Cited

OTHER PUBLICATIONS

Koehnlein et al., "Increased cardiac troponin T and C-reative protein levels in end-stage renal disease are associated with obstructive sleep apnea," Clin Nephrol, Jan. 2007, pp. 50-58, vol. 71, No. 1.
Koerbin et al., "The comparative analytical performance of four troponin I assays at low concentration," Ann Clin. Biochem., 2005, pp. 19-23, vol. 42.
Larue et al., "Cardiac-Specific Immunoenzymaometric Assay of Troponin I in the Early phase of Acute Myocardial Infarction," Clinical Chemistry, 1993, pp. 972-979, vol. 39.
Lecaptain et al., "Two-Beam Fluorescence Cross-Correlation Spectroscopy in an Electrophoretic Mobility Shift Assay," Anal. Chem., 2002, 1171-1176, vol. 74.
Lecaptain et al.: "Characterization of DNA-protein complex by capillary electrophoresis-single molecule fluorescence correlation spectroscopy," Analyst, 2001, pp. 1279-1284, vol. 126.
Lexington Medical Center. Mycardial infarction redefined. NewsPath, May 2001.
Li et al., "Ultrasensitive Coincidence Fluorescence Detection of Single DNA Molecules," Anal. Chem., 2003, pp. 1664-1670, vol. 75.
Loscher et al., Counting of Single Protein Molecules at Interfaces and Application of This Technique in Early-Stage Diagnosis, Anal. Chem, 1998, pp. 3202-3205, vol. 70.
Lucey et al., "Type 1 and Type 2 Cytokine Dysregulation in Human Infectious, Neoplastic and Inflammatory Diseases," Clinical Microbiology Reviews, Oct. 1996, pp. 532-562, vol. 9, No. 4.
Ma et al., "Single-molecule immunoassay and DNA diagnosis," Electrophoresis, 2001, pp. 421-426, vol. 22.
Mair, Johannes, "Cardiac troponin I and Troponin T: Are enzymes still relevant as cardiac markers?" Clinica Chimica Acta, 1997, NR. 1, pp. 99-115, vol. 257.
Missov et al., Circulating Cardiac Troponin I in Severe Congestive Heart Failure, Circulation, 1997, pp. 2953-2958, vol. 96.
Nalefski et al.: "Single-molecule counting of macromolecular complexes in real time: a novel approach to quantify transcription factor—DNA and antibody-antigen interactions," FASEB Journal, 2004, 2 pages, vol. 18, No. 8: C176.
Nguyen et al., "Detection of Single Molecules of Phycoerythrin in Hydrodynamically Focused Flows by Laser-Induced Fluorescence," Anal. Chem., 1987, pp. 2158-2161, vol. 59.
Oh et al., "E of a dual monoclonal solid phase and a polyclonal detector to create an immunoassay for the detection of human cardiac troponin I," Clin. Biochem., 2000, pp. 255-262, vol. 33.
Ohman et al., "Cardiac troponin T levels for risk stratification in acute mycardial ischemia," The New England Journal of Medicine, 1997, pp. 1333-1341, vol. 335.
Panchuk-Voloshina et al.: "Alexa Dyes, a Series of New Fluorescent Dyes that Yield Exceptionally Bright, Photostable Conjugates," J. Histochem Cytochem, 1999, pp. 1179-1188, vol. 47, No. 9.
Panteghini et al., "Evaluation of imprecision for cardiac troponin assays at low range concentrations," Clinical Chemistry, 2004, pp. 327-332, vol. 50.
Panteghini, Mauro, "Role and importance of biochemical markers in clinical cardiology," European Heart Journal, 2004, pp. 1187-1196, vol. 25.
Panteghini, Mauro, "The interfering component in cardiac troponin I immunoassays: need for further experimental evidence," Clin Chem., 2004, pp. 676-677, vol. 50.
Park, Richard, "Addressing Unmet Needs in Assay Development," Medical Device Link, Mar. 2007, pp. 1-4.
Peck et al., "Single-molecule fluorescence detection: Autocorrelation criterion and experimental realization with phycoerythrim," Proc. Natl. Acad. Sci. USA, Jun. 1989, pp. 4087-4091, vol. 86.
Phillips et al., "Application of single molecule technology to rapidly map long DNA and study the conformation of stretched DNA", Nucleic Acids Res., 2005, pp. 5829-5837, vol. 33, No. 18.
Rigler, "Fluorescence correlations, single-molecule detection and large number screening," Applications in Biotechnology J. Biotechnol., 1995, pp. 177-186, vol. 4.
Sabatine et al., "Detection of acute changes in circulating troponin in the setting of transient stress test-induced myocardial ischaemia ing an ultrasensitive assay: results from TIMI 35," Cur Heart J., Jan. 2009 (ePub Nov. 8, 2008).
Sato et al., "Biochemical markers of myocyte injury in heart failure," Heart (British Cardiac Society), 2004, pp. 1110-1113, vol. 90.
Sauer et al., "Detection and identification of individual antigen molecules in human serum with pulsed semiconductor lasers," Appl. Phys. B., 1997, pp. 427-431, vol. 65.
Schiffer et al.: "High resolution proteome/peptidome analysis of body fluids by capillary electrophoresis coupled with MS," Proteomics (2006) V. 6, pp. 5615-5627.
Schulz et al., "Cardiac troponin I: A potential marker of exercise intolerance in patients with moderate heart failure," American Heart Journal, 2002, pp. 351-358, vol. 144.
Shera et al., "Detection of single fluorescent molecules," Chemical Physics Letters, Nov. 23, 1990, pp. 553-557, vol. 174, No. 6.
Shortreed et al., "High-Throughput Single-Molecule DNA Screening Based on electrophoresis," Anal. Chem., 2000, pp. 2879-2885, vol. 72.
Sidransky, David, "Emerging Molecular Markers of Cancer," Nature Reviews: Cancer, Mar. 2002, pp. 210-219, vol. 2.
Soper et al., "Photon Burst Detection of Single Near-Infrared Fluorescent Molecules," Anal. Chem., 1993, pp. 740-747, vol. 65.
Soper et al., "Single-molecule detection in the near-IR using continuos wave diode laser excitation with an avalanche photon detector," Applied Spectroscopy, 1998, pp. 1-6, vol. 52.
Stiegler et al., "Lower cardiac tropoinin T and I results in heparin-plasma than in serum," Clinical Chemistry, 2000, pp. 1338-1344, vol. 46.
Tanaka et al., "Protein and Polymer Analyses up to m/z 100 000 by Laser Ionization Time-of-flight Mass Spectrometry," Rapid Commun. Mass. Spect., 1988, pp. 151-153, vol. 2.
Thomas, Ma et al., "A review of troponin assay performance in Wales: can the same (method-dependent) decision limits be used in different sites?" Ann. of Clinical Biochemistry, British Medical Association, London, GB, Sep. 1, 2005, pp. 351-356, vol. 42, No. 5.
Todd, J. et al., "Ultrasensitive flow-based immunoassays ing single-molecule counting," Clinical Chemistry, American Association for Clinical Chemistry, Washington DC, Nov. 1, 2007, pp. 1990-1995, vol. 53, No. 11.
Achar et al., "Diagnosis of acute coronary syndrome," American Family Physician, 2005, pp. 119-1265, vol. 72.
Adams et al., "Cardiac troponin I.A. marker with high specificity for cardiac injury," Circulation, 1993, pp. 101-106, vol. 88.
Adams et al., "Comparable detection of acute myocardial infarction by creatine kinase MB isoenzyme and cardiac troponin I.," Clinical Chemistry, 1994, pp. 1291-1295, vol. 40.
Al-Awadhi et al., Singapore Med. J., 2007, pp. 847-849, vol. 48.
Alexa Fluor Succinimidyl Esters. Invitrogen. Revised Jan. 4, 2006; 1-5.
Alexa Fluor Dyes Handbook. Simply the Best and Brightest: Fluorescent Dyes and Conjugates. Invitrogen. Copyright 2005. Molecular Probes. 1-33.
Ambrose et al., "Single Molecule Fluorescence Spectroscopy at Ambient Temperature," Chemical Reviews, 1999, pp. 2929-2956, vol. 99.
Anazawa et al., "Electrophoretic Quantitation of Nucleic Acids Without Amplification by Single Molecule Imaging," Anal. Chem, 2002, pp. 5033-5038, vol. 74.
Antman et al., "Cardiac-specific troponin I levels to predict the risk of mortality in patients with acute coronary syndromes," The New England Journal of Medicine, 1996, pp. 1342-1349, vol. 335.
Apple et al., "The diagnostic utility of cardiac biomarkers in detecting myocardial infarction," Clinical Cornerstone 2005, pp. S25-S30, vol. 7.

(56) References Cited

OTHER PUBLICATIONS

Apple et al., "Validation of the 99th Percentile Cutoff Independent of Assay Imprecision (CV) for Cardiac Troponin monitoring for Ruling out Myocardial Infarction," Clinical Chemistry, 2005, pp. 2198-2200, vol. 51.
Babuin et al., "Troponin:the biomarker of choice for the detection of cardiac injury," Canadian Medical Association Journal, 2005, pp. 1191-1202, vol. 173.
Becker et al., "Three-Dimensional Photogrammetric Particle-Tracking Velocimetry," Preparing for the Future, 1995, 7 pages, vol. 5, No. 3; available at http://esapub.esrin.esa.it/pff/pffv5n3/beckv5nc.htm.
Bieschke et al., "Ultrasensitive detection of pathological prion protein aggregates by dual-color scanning for intensely fluorescent targets," Pro. Natl. Acad. Sci., May 9, 2000, pp. 5468-5473, vol. 97, No. 10.
Borrebaeck, Carl A.K., Antibody Engineering. Second Edition, Oxford University Press, Oxford, 1995, 11 pages.
Bouchon et al., "Cutting edge: inflammatory responses can be triggered by TREM-1, a novel receptor expressed on neutrophils and monocytes," The Journal of Immunology, 2000, pp. 4991-4995, vol. 164.
Braunwald et al., "ACC/AHA 2002 guideline update for the management of patients with unstable angina and non-ST-segment elevation mycardial infarction-A report of the American College of Cardiology/American Heart Association task force on practice guidelines (Committee on the Management of Patients with Unstable Angina)," American College of Cardiology and the American Heart Association, 2002.
Brinkmeier et al., "Two-beam cross-correlation: a method to characterize transport phenomena in micrometer-sized structures," Anal. Chem., 1999, pp. 609-616, vol. 71.
Buisson et al., "Biochemical markers of my cardial injury," Available at http://ww.ampath.co.za/Documents/biochemicalMarkers.pdf. Accessed Sep. 20, 2007.
Castro et al., "Fluorescence Detection and Size Measurement of Single DNA Molecules," Anal. Chem., 1993, pp. 849-852, vol. 65.
Castro et al., "Single molecule detection: applications to ultrasensitive biochemical analysis," Applied Optics, Jun. 20, 1995, pp. 3218-3222, vol. 34, No. 18.
Castro et al., "Single-molecule detection of specific nucleic acid sequences in unamplified genomic DNA," Anal. Chem., 1997, pp. 3915-3920, vol. 69.
Castro et al., "Single-Molecule Electrophoresis," Anal. Chem., 1995, pp. 3181-3186, vol. 67.
Castro et al., "Ultrasensitive, direct detection of a specific DNA sequence of Bacillus anthracis in solution," Analyst, 2000, pp. 9-11, vol. 125.
Cayley: "Diagnosing the case of chest pain," American Family Physician, 2005, pp. 2012-2021, vol. 72.
Chan et al., "DNA Mapping Using Microfluidic Stretching and Single-Molecule Detection of Fluorescent Site-Specific Tags," Genome Res., 2004, pp. 1137-1146, vol. 14.
Chen et al., "Single-Molecule Detection in Capillary Electrophoresis: Molecular Shot Noise as a Fundamental Limit to Chemical Analysis," Anal. Chem., 1996, pp. 690-696, vol. 68.
Cohen et al.: "The Renal TGF-beta System in the db/db Mouse Model of Diabetic Nephropathy," Exp. Nephrol., 1998, pp. 226-233, vol. 6.
Colonna, Marco, "TREMS in the Immune System and Beyond," Nature Reviews: Immunology, Jun. 2003, pp. 445-453, vol. 3.
CSIRO Australia, "Image motion, tracking and registration," CMIS Research—Image Analysis, Available at http://www.cmis.csiro.aul/AP/Motion. Accessed Jan. 24, 2005, pp. 1-3.
D'Antoni et al., "Rapid quantitative analysis using a single molecule counting," Anal. Chem., 2006, pp. 97-109, vol. 352.
Diderholm et al., "The prognostic and therapeutic implications of increased troponin T levels and ST depression in unstable coronary artery disease: the FRISC II invasive tropoinin T electrocardiogram substudy," American Heart Journal, 2002, pp. 760-767, vol. 143.
Dovichi et al., "Laser-Induced Fluorescence of Flowing Samples as an Approach to Single-Molecule Detection in Liquids," Anal. Chem., 1984, pp. 348-354, vol. 56.
Dunbar et al., "Quantitative multiplexed detection of bacterial pathogens: DNA and protein applications of Luminex LabMap system," J. Microbiol Methods. 2003, pp. 245-252, vol. 53.
Eder et al., "Transforming Growth Factor-Beta1 and Beta2 in Serum and Urine from Patients with Bladder Carcinoma," The J. of Urology, Sep. 1996, pp. 953-957, vol. 156.
Effenhauser et al., "Integrated Capillary Electrophoresis on Flexible Silicone Microdevices: Analysis of DNA Restriction Fragments and Detection of Single DNA Molecules on Microchips," Anal. Chem., 1997, pp. 3451-3457, vol. 69.
Eryol et al., "Should Troponin-T Be Assessed During Exercise Stress Testing in Patients with Stable Angina Pectoris?" Anadolu Kardiyol Der., 2002, pp. 132-137, vol. 2.
Eskelinen et al., "A New Tumor Marker MCA in Breast Cancer Diagnosis," Anticancer Res., 1988, pp. 665-668, vol. 8.
Etzioni et al., "The Case for Early Detection," Nature Reviews: Cancer, Apr. 2003, pp. 243-252, vol. 3.
Ferrieres et al., "Human cardiac troponin I: precise identification of antigenic epitopes and prediction of secondary structure," Clinical Chemistry, 1998, pp. 487-493, vol. 44.
Fister et al., "Counting Single Chromphore Molecules for Ultrasensitive Analysis and Separations on Microchip Devices," Anal. Chem., 1998, pp. 431-437, vol. 70.
Gaze et al., "Cardiac Troponins as Biomarkers of Drug and Toxin Induced Cardiac Toxicity and Cardioprotection," Expert Opin. Drug Metabl. Toxocol., 2005, pp. 715-725, vol. 1.
Giannitsis et al., "Admission tropoinin T level predicts clinical outcomes, TIMI flow, and mycardial tissue perlion after primary percutaneo intervention for acute ST-segment elevation mycoardial infarction," Circulation, 2001, pp. 630-635, vol. 104.
Gibot et al., "Soluble Triggering Receptor Expressed on Myeloid Cells and the Diagnosis of Pneumonia," The New England Journal of Medicine, Jan. 29, 2004, pp. 451-458, vol. 350.
Glenn Research Center, NASA, "Particle Image Velocimetry," Available at http://www.grc.nasa.gov/www/Optlinstr/piv/background.htm and associated web pages. Accessed Jan. 26, 2005, pp. 1-3.
Goix, Dr. P., "Fulfilling the promise of biomarkers in drug discovery and development," Drug Discovery + International, Apr./May 2007, pp. 6-7.
Goix, Philippe, Slides from presentation at clinical biomarkers summit, Coronado, CA, Mar. 29-31, 2006, 29 pages.
Golde, Todd E., "Alzheimer disease therapy: Can the amyloid cascade be halted?," J. Clin. Invest., 2003, pp. 11-18, vol. 11.
Guenard et al., "Two-Channel Sequential Single-Molecule Measurement," Anal. Chem., 1997, pp. 2426-2433, vol. 69.
Guide to Amine-Reactive Probes., Revised Oct. 13, 2005, 9 pages.
Upatnieks et al., "A kilohertz frame rate cinemagraphic PIV system for laboratory-scale turbulent and unsteady flows," Experiments in Fluids, 2002, pp. 87-98, vol. 32.
Van Orden et al., Single-Molecule Identification in Flowing Sample Streams by Fluorescence Burst Size in Intraburst Fluorescence Decay Rate, Anal. Chem., 1998, pp. 1444-1451, vol. 70.
Van Wissen et al., "Differential hs-CRP reduction in patients with familial hypercholesterolemia treated with aggressive or conventional statin therapy," Atherosclerosis, Dec. 2002, pp. 361-366, vol. 165, No. 2.
Von Zur Muhlen et al., "Evaluation of Urine Proteome Pattern Analysis for Its Potential to Reflect Coronary Artery Atherosclerosis in Symptomatic Patients," J. Proteome Res., 2009, pp. 335-345, vol. 8.
Wabuyele et al., "Single molecule detection of double-stranded DNA in poly(methylmethacrylate) and polycarbonate microfluidic devices," Electrophoresis, 2001, pp. 3939-3948, vol. 22.
Wallace et al., "Serum Troponins as Biomarkers of Drug-Induced Cardiac Toxicity," Toxicologic Pathology, 2004, pp. 106-121, vol. 32.
Willneff, J., "A Spatio-Temporal Matching Algorithm for 3D Particle Tracking Velocimetry," a dissertation submitted to the Swiss Federal Institute of Technology Zurich for the degree of Doctroal of

(56) References Cited

OTHER PUBLICATIONS

Technical sciences (English abstract), Sep. 2003, Diss. Eth No. 15276, pp. 1-5; Available at http://e-collection.ethbib.ethz.ch/ecol-pool/diss/abstracts/p15276.pdf.
Wu et al., "Development and Preliminary Clinical Validation of a High Sensitivity Assay for Cardiac Tropoin using a Capillary Flow (Single Molecule) Fluorescence Detector," Clinical Chemistry, 2006, pp. 2157-2159, vol. 52.
Wu et al., "Development and preliminary clinical validation of a high sensitivity assay for cardiac troponin using a capillary flow (single molecule) fluorescence detector," Poster presented at Oak Ridge conference. Apr. 22-22, 2006, 1 page.
Young, Karen, "Singulex Developing Troponin Test for earlier detection of AMI," Medical Device Daily, Dec. 13, 2006, pp. 1-2, vol. 10, No. 238.
Zetheli et al., "Troponin I as a predictor of coronary heart disease and morality in 70-year-old mend: a community-based cohort study," Circulation, Feb. 28, 2006, pp. 1071-1078, vol. 113, No. 8.
Zhu et al., "Fluorescence Multiplexing with Time-Resolved and Spectral Discrimination Using a Near-IR Detector," Anal. Chem, 2003, pp. 2280-2291, vol. 75.
Zimmerli et al., "Urinary Proteomic Biomakers in Coronary Artery Disease," Mol. Cell Proteomics, Feb. 2008, pp. 290-298, vol. 7, No. 2.
Puskas, U.S. Appl. No. 60/613,881, entitled "Continuous wave single particle detector," filed Sep. 28, 2004, 72 pages.
Puskas, U.S. Appl. No. 60/624,785, entitled "Sandwich assay for detection of individual molecules," filed Oct. 29, 2004, 3 pages.
Puskas, Robert Steven, U.S. Appl. No. 10/718,194, entitled: "Preparation of defined highly labeled probes," filed Nov. 19, 2003.
Puskas, Robert Steven, U.S. Appl. No. 10/720,047, entitled: "Charge and mass tags for detection and analysis," filed Nov. 19, 2003.
Puskas et al., U.S. Appl. No. 11/048,660, entitled: "System and Methods for Sample Analysis," filed Jan. 28, 2005.
Goix et al., U.S. Appl. No. 11/767,196, entitled: "System and Method for Sample Analysis," filed Jun. 22, 2007.
Goix, Philippe J., U.S. Appl. No. 11/784,186, entitled "Methods and Compositions for Highly Sensitive Analysis of Markers," filed Apr. 4, 2007, 124 pages.
Goix, Philippe J., U.S. Appl. No. 11/830,762, entitled "Methods and Compositions for Highly Sensitive Detection of Molecules," filed Jul. 30, 2007.
Puskas et al., U.S. Appl. No. 11/838,114, entitled: "System and Method for Sample Analysis," filed Aug. 13, 2007.
Goix, Philippe J., U.S. Appl. No. 12/060,997, entitled: "Methods and Compositions for Highly Sensitive Analysis of Markers," filed Apr. 2, 2008, 167 pages.
Puskas et al., U.S. Appl. No. 12/276,277, entitled: "System and Method for Sample Analysis," filed Nov. 21, 2008.
Goix, Philippe J., U.S. Appl. No. 12/731,500, entitled "Methods and Compositions for Highly Sensitive Detection of Molecules," filed Mar. 25, 2010.
Todd et al., "Specificity of a High-Sensitivity Cardiac Troponin I Assay Using Single-Molecule-Counting Technology," Clinical Chemistry, 2009, pp. 196-198, vol. 55, No. 1.
John Allan Todd, U.S. Appl. No. 61/332,081, entitled: "Methods for Diagnosing, Staging, Predicting Risk for Developing and Identifying Treatment Responders for Rheumatoid Arthritis," filed May 6, 2010.
John Allan Todd, U.S. Appl. No. 61/428,500, entitled: "Methods for Diagnosing, Staging, Predicting Risk for Developing and Identifying Treatment Responders for Rheumatoid Arthritis," filed Dec. 30, 2010.
John Allan Todd, U.S. Appl. No. 61/444,702, entitled: "Methods for Diagnosing, Staging, Predicting Risk for Developing and Identifying Treatment Responders for Rheumatoid Arthritis," filed Feb. 19, 2011.
Lubberts, Erik, "Th17 cytokines and arthritis," Seminars in Immunopathology, 2010, pp. 43-53, vol. 32, No. 1.
Alex et al., "Multiplex serum cytokine monitoring as a prognostic tool in rheumatoid arthritis," Clinical and Experimental Rheumatology, 2007, pp. 584-592, vol. 25.
Barnes, Peter J., "The Cytokine Network in Chronic Obstructive Pulmonary Disease," Am. J. Respir. Cell Mol. Biol., 2009, pp. 631-638, vol. 41.
Brynskov et al., "Increased concentrations of interleukin 1β, interleukin-2, and soluble interleukin-2 receptors in endoscopical mucosal biopsy specimens with active inflammatory bowel disease," Gut, 1992, pp. 55-58, vol. 33.
Schultze et al., "Ultrasensitive Cross-species Measurement of Cardiac Troponin-I Using the Erenna Immunoassay System," Toxicologic Pathology, 2008, pp. 777-782, vol. 36.
Singulex, Erenna IL-17A Immunoassay Kit data sheet, 2006, 3 pages.
Singulex, Erenna IL-1β Immunoassay Kit, 2006, 3 pages.
Tchetverikov et al., "MMP profile in paired serum and synovial fluid samples of patients with rheumatoid arthritis," Annual Rheumatology Disease, 2004, pp. 881-883, vol. 63.

\* cited by examiner

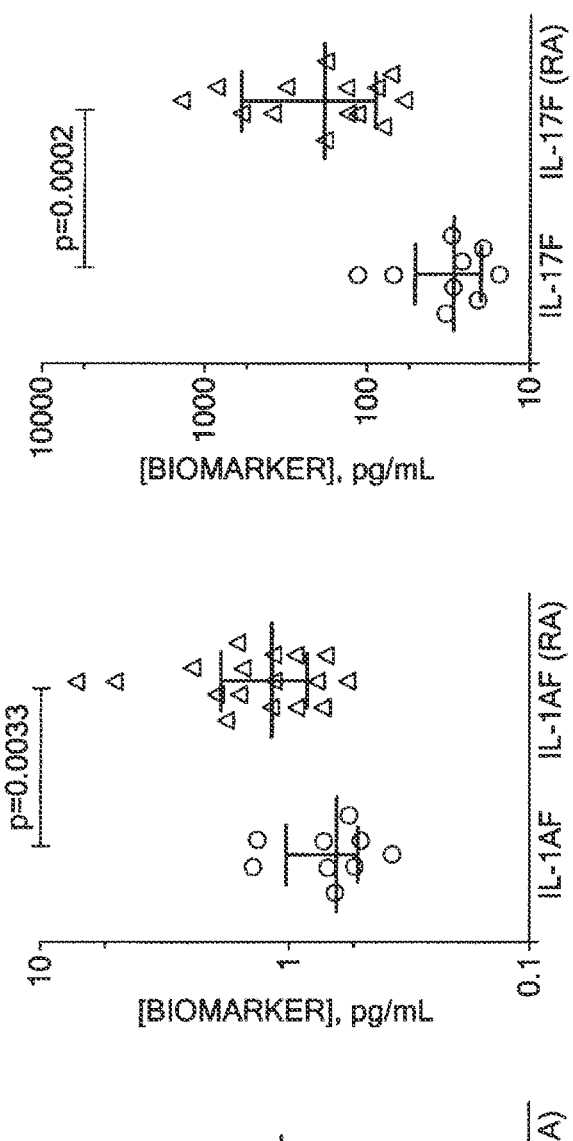

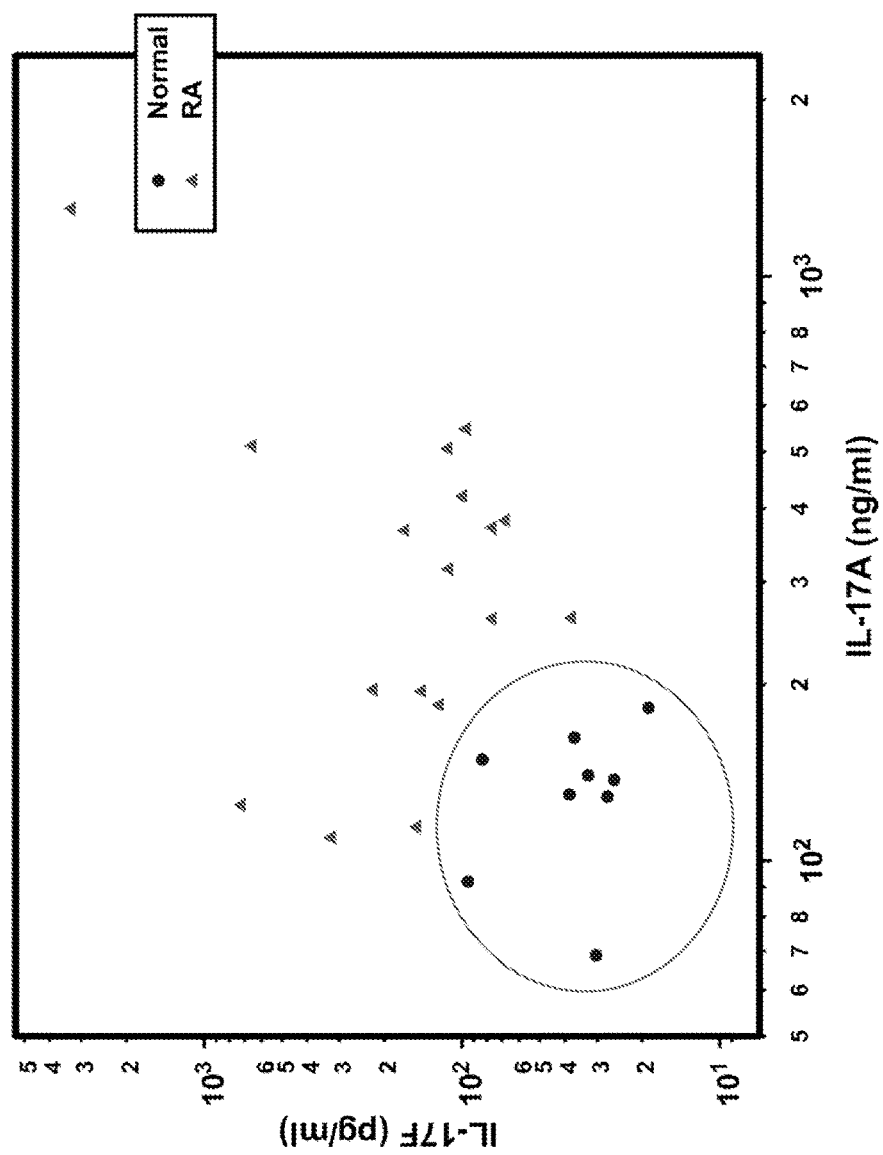

METHODS FOR DIAGNOSING, STAGING, PREDICTING RISK FOR DEVELOPING AND IDENTIFYING TREATMENT RESPONDERS FOR RHEUMATOID ARTHRITIS

This application is a continuation of U.S. patent application serial No. 13/102,683, filed May 6, 2011, now abandoned, which claims the benefit of U.S. Provisional Patent Application Serial No. 61/332,081, filed May 6, 2010; U.S. Provisional Patent Application Serial No. 61/428,500, filed Dec. 30, 2010; and U.S. Provisional Patent Application Serial No. 61/444,702, filed Feb. 19, 2011. Each of the above-referenced applications are incorporated by reference herein in their entirety.

BACKGROUND

Rheumatoid Arthritis (RA) is characterized by synovial inflammation and destruction of joint cartilage and bone. Such destruction is caused in part by the ongoing synthesis of proinflammatory cytokines and matrix metalloproteinases. Autoimmune diseases, such as RA have been classically viewed as Th1 (CD4+ T helper cell-induced; interferon-gamma, for example, is produced, which activates the bactericidal activities of macrophages and induces B-cells to make opsonizing (coating) antibodies, leading to cellular immunity) and not Th2 (CD4+ T helper cell-induced; interleukin 4, for example, is released, which results in the activation of B-cells to make neutralizing antibodies, leading to humoral immunity) disorders. However, recent studies have brought this thought into questions (Lubberts; Seminars in Immunopathology 32(1), 43-53 (2010)). For example, IL-17a (a proinflammatory cytokine) is present at sufficient concentrations in the synovial fluid of RA patient joints that it can be detected. However, this and other cytokines cannot be detected in serum or plasma obtained from the same patients. There is a need to detect biomarkers in serum or plasma that are related to RA and other inflammatory disorders (e.g., Crohn's Disease, Inflammatory Bowel Disease (IBD), ulcerative colitis, psoriasis, Chronic Obstructive Pulmonary Disease (COPD)) so that RA can be more readily or effectively diagnosed and staged, risk for developing RA or other inflammatory disorder can be more readily or effectively assessed, and patients who are responders and non-responders to RA therapy can be more readily or effectively identified.

SUMMARY OF THE INVENTION

In an aspect, the disclosure provides methods for predicting the risk for developing RA or other inflammatory disorders (e.g., Crohn's Disease, Inflammatory Bowel Disease (IBD), ulcerative colitis, psoriasis, Chronic Obstructive Pulmonary Disease (COPD)) in a subject, comprising obtaining a sample from the subject, determining a concentration of each of IL-17A (Interleukin 17A), IL-17A/F (Interleukin 17A/17F heterodimer), and IL-17F (Interleukin 17F), and optionally one or more of IL-1β (Interleukin 1-beta), IL-6 (Interleukin 6), totMMP-9 (total precursor and active matrix metallopeptidase 9 (or gelatinase B)), proMMP-9 (precursor protein of matrix metallopeptidase 9), cTnI (cardiac troponin I), and combinations thereof in the sample, wherein when the subject has a concentration of IL-17A, IL-17A/F and/or IL-17F greater than about 0.18 pg/ml, 1.35 pg/ml and 116 pg/ml, respectively, the subject is predicted to have a greater than normal risk of developing RA or other inflammatory disorders. In certain aspects, subject IL-17A, IL-17A/F and/or IL-17F biomarker concentrations are compared to average biomarker concentrations for healthy volunteers, and in aspects age- and/or gender-matched healthy volunteers, to predict whether they have a greater than normal risk of developing RA or other inflammatory disorders. In other aspects, additional biomarker (e.g., IL-1β, IL-6, totMMP-9, proMMP-9, cTnI) concentrations are determined and utilized to predict whether a subject has a greater than normal risk of developing RA or other inflammatory disorders. In some aspects values are used, and in others comparisons to average biomarker concentrations for healthy volunteers, and in aspects age- and/or gender-matched volunteers are utilized.

In another aspect, the disclosure provides methods for determining the likelihood of developing RA or other inflammatory disorders in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and/or IL-17F greater than about 0.18 pg/ml, 1.35 pg/ml and 116 pg/ml, respectively, the subject has an increased likelihood of developing RA or other inflammatory disorders. In certain aspects, subject IL-17A, IL-17A/F and/or IL-17F biomarker concentrations are compared to average biomarker concentrations for healthy volunteers, and in aspects age- and/or gender-matched healthy volunteers, to determine the likelihood of the subject developing RA. In other aspects, additional biomarker (e.g., IL-1β, IL-6, totMMP-9, proMMP-9, cTnI) concentrations are determined and utilized to determine the likelihood of the subject developing RA or other inflammatory disorders. In some aspects values are used, and in others comparisons to average biomarker concentrations for healthy volunteers, and in aspects age- and/or gender-matched volunteers are utilized.

In another aspect, the disclosure provides methods for identifying an RA or other inflammatory disorder patient who responds to therapy, comprising obtaining a first sample from the RA patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the RA or other inflammatory disorder patient, obtaining a second sample from the RA patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the RA patient has a first concentration of IL-17A, IL-17A/F and/or IL-17F greater than about 0.18 pg/ml, 1.35 pg/ml and 116 pg/ml, respectively, and a second concentration of IL-17A, IL-17A/F and/or IL-17F less than about 0.18 pg/ml, 1.35 pg/ml and 116 pg/ml, respectively, the RA or other inflammatory disorder patient is identified as RA or other inflammatory disorder patients who responds to therapy.

In another aspect, the disclosure provides methods for predicting the rate of inflammatory disease progression in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the concentration of none, one or more than one of IL-17A is greater than 0.18 pg/ml, IL-17-F is greater than 116 pg/ml, or IL-17A/F is greater than 1.35 pg/ml, and wherein when the concentration of one, one or more or at least two of IL-1β is less than 1.1. pg/ml, totMMP-9 is less than 5.0 ng/ml, or IL-6 is greater than 1.0 pg/ml, the subject is predicted to have a slow rate, medium rate or high rate of inflammatory disease progression.

In another aspect, the disclosure provides methods for predicting the likelihood of inflammatory disease remission in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the concentration of none, one or more than one of IL-17A is greater than 0.18 pg/ml, IL-17-F is greater than 116 pg/ml, or IL-17A/F is greater than 1.35 pg/ml, and wherein when the concentration of one, one or more or at least two of IL-1β is less than 1.1. pg/ml, totMMP-9 is less than 5.0 ng/ml, or IL-6 is greater than 1.0 pg/ml, the subject is predicted to have a high likelihood, medium likelihood or a low likelihood of inflammatory disease remission.

In another aspect, the disclosure provides methods for determining the severity of inflammatory disease in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the concentration of one or more of IL-17A is greater than 0.18 pg/ml, IL-17-F is greater than 116 pg/ml, or IL-17A/F is greater than 1.35 pg/ml, and wherein when the concentration of none, one, one or more, or two or more or one of IL-1β is less than 1.1. pg/ml, totMMP-9 is less than 5.0 ng/ml, or IL-6 is greater than 1.0 pg/ml, the subject is determined to have mild, moderate or severe inflammatory disease.

For all of the above aspects related to predicting the rate of inflammatory disease progression, predicting the likelihood of inflammatory disease remission, or determining the severity of inflammatory disease, the inflammatory disease is selected from the group consisting of RA, Crohn's Disease, IBD, ulcerative colitis, psoriasis, and COPD.

In certain aspects, subject IL-17A, IL-17A/F and/or IL-17F biomarker concentrations are compared to average biomarker concentrations for healthy volunteers, and in aspects age- and/or gender-matched healthy volunteers, to identify RA or other inflammatory disorder patients who respond to therapy. In other aspects, additional biomarker (e.g., IL-1β, IL-6, totMMP-9, proMMP-9, cTnI) concentrations are determined and utilized to identify RA or other inflammatory disorder patients who respond to therapy. In some aspects values are used, and in others comparisons to average biomarker concentrations for healthy volunteers, and in aspects age- and/or gender-matched volunteers are utilized.

In another aspect, the disclosure provide method for determining inflammatory disease in a patient. The method includes detecting the concentration of more or more the following markers in a patient sample: IL-17A, IL-17F, IL-17A/F, IL-1β, IL-6, totMMP-9, proMMP-9, and cTnI, comparing the level of the one or more markers to the level in a normal population of healthy volunteers; and determining that the patient has inflammatory disease when the concentration of IL-17A, IL-17F, IL-17A/F, IL-6, or cTnI are elevated relative to the normal population, or totMMP-9, proMMP-9, or IL-1β are decreased relative to the normal population. In certain aspects, the disease is RA and the one or more markers include the combination of IL-17F & IL-17A, the combination of IL-17A and IL-17 A/F, or the combination of IL-17F and IL-17 A/F.

Other aspects and embodiments of the invention will become apparent to those of skill in the art in view of the following detailed description.

BRIEF DESCRIPTION OF THE DRAWINGS

FIGS. 2A-2I provide a larger-scale views of select results illustrated in FIG. 1. The three hash marks through each data set represent mean and upper and lower quartile divisions (rather than mean and one standard deviation above and below the mean).

FIG. 5 shows that the combination of IL-17F & IL-17A as biomarkers for RA were 100% predictive of disease.

DETAILED DESCRIPTION OF THE INVENTION

Figure 1:
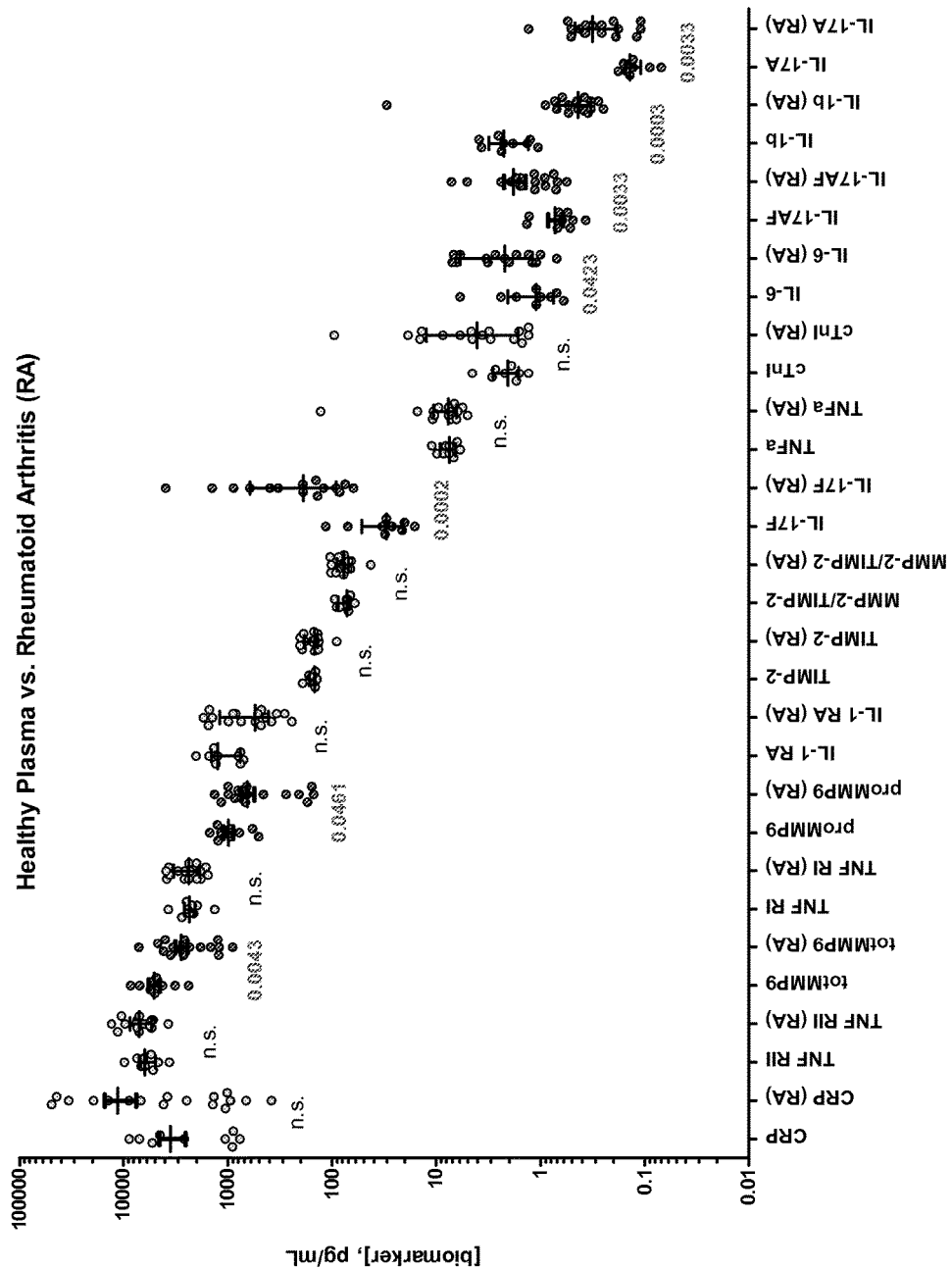
FIG. 1 illustrates various biomarker levels in RA patients versus healthy volunteers. The three hash marks through each data set represent mean and one standard deviation above and below the mean. Concentrations of several markers are significantly elevated or attenuated in RA patients (P-values are indicated).
Figure 2F:
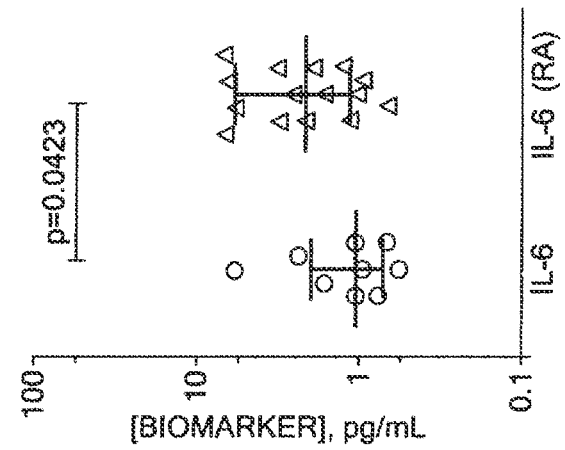
Figure 2E:
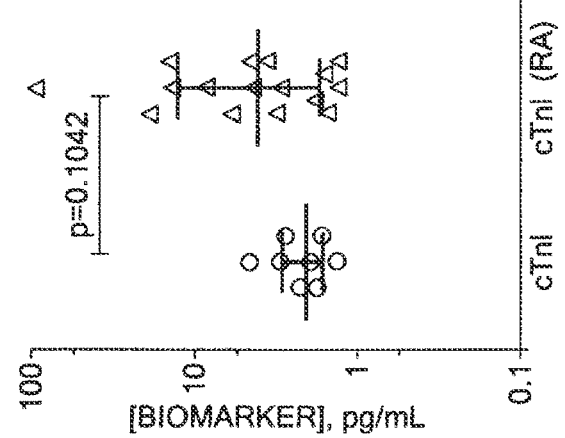
Figure 2D:
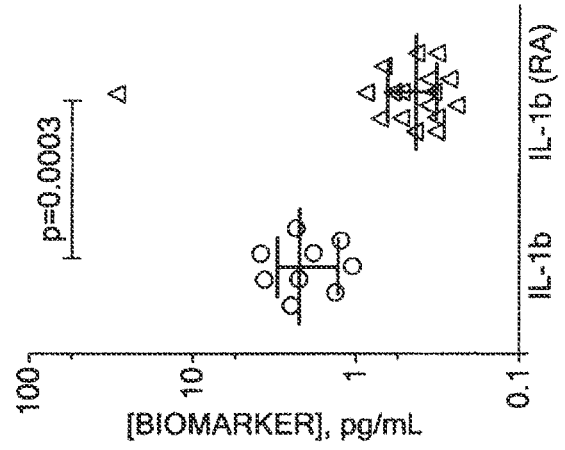
Figures 2G, 2H, 2I:
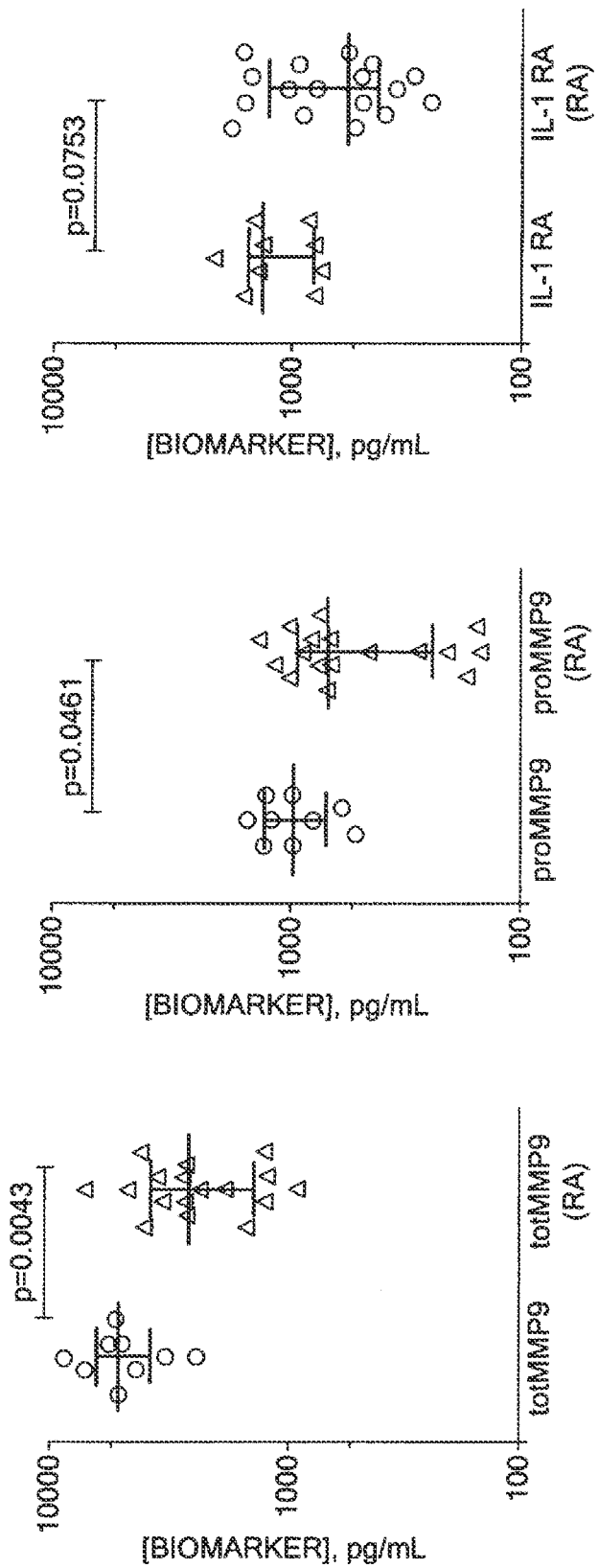

All publications, patent applications, patents and other references mentioned herein, if not otherwise indicated, are explicitly incorporated by reference.

Unless otherwise defined, the technical and scientific terms used herein have the same meaning as commonly understood by one of ordinary skill in the art. Expansion and clarification of some terms are provided herein.

As used herein, the term "subject" refers to a mammal that can be afflicted by a rheumatoid arthritis, but may or may not have such a disease. Typically, the terms "subject" and "patient" are used herein interchangeably in reference. In various embodiments, the subject is a human.

As used herein, the term "sample" is taken broadly to include any sample suitable for the methods described herein. Typically, the sample is a biological sample such as, for example, a biological fluid. Such fluids can include, without limitation, bronchoalveolar lavage fluid (BAL), blood, serum, plasma, urine, nasal swab, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the target particle of interest. Other similar specimens such as cell or tissue culture or culture broth are also of interest. In some embodiments, the sample is a blood sample. In some embodiments the sample is a plasma sample. In some embodiments the sample is a serum sample.

As used herein, the term "healthy volunteer average concentrations" refers to the average concentration of the various biomarkers described herein for at least two subjects who do not have RA (e.g., HV). Preferably, average concentration values are calculated from biomarker concentrations measured in larger groups of HVs. Healthy volunteer average concentrations are provided herein, but one of skill in the art may also measure biomarker concentrations in one or more populations of subjects lacking RA utilizing an apparatus capable of sensitively measuring the concentrations of biomarkers described herein and calculating the average values for each biomarker in such HV populations.

As used herein, the term "therapy" refers to the administration of any medical treatment (e.g., pharmaceuticals) or interventional treatment (e.g., surgery) to affect RA or the biomarkers relevant to RA described herein.

As used herein, the term "substantially the same as" refers to ±about 25%, ±about 20%, ±about 15%, ±about 10%, ±about 5%, ±about 3%, ±about 2%, or ±about 1% of the healthy volunteer average concentrations of a biomarker. In some aspects "substantially the same as" refers to ±about 20%, ±about 15%, ±about 10%, or ±about 5%, ±about 3%, ±about 2%, or ±about 1% of the healthy volunteer average concentrations of a biomarker. In some aspects "substantially the same as" refers to ±about 15%, ±about 10%, ±about 5%, ±about 3%, ±about 2%, or ±about 1% of the healthy volunteer average concentrations of a biomarker. In some aspects "substantially the same as" refers to ±about 10%, ±about 5%, ±about 3%, ±about 2%, or ±about 1% of the healthy volunteer average concentrations of a biomarker. In some aspects "substantially the same as" refers to ±about 5%, ±about 3%, ±about 2%, or ±about 1% of the healthy volunteer average concentrations of a biomarker. In some aspects "substantially the same as" refers to ±about 3%, ±about 2%, or ±about 1% of the healthy volunteer average concentrations of a biomarker. In some aspects "substantially the same as" refers to ±about 2%, or ±about 1% of the healthy volunteer average concentrations of a biomarker. In some aspects "substantially the same as" refers to ±about 1% of the healthy volunteer average concentrations of a biomarker.

As used herein, the term "CV" refers to the coefficient of variance. In some aspects "substantially the same as" refers to ±about 10%, ±about 5%, ±about 3%, ±about 2%, or ±about 1% of the healthy volunteer average concentrations of a biomarker. In some aspects "substantially the same as" refers to ±about 5%, ±about 3%, ±about 2%, or ±about 1% of the healthy volunteer average concentrations of a biomarker.

As used herein, the term "average CV" refers to average of the coefficient of variance obtained for all samples tested in triplicate.

As used herein, the term "LoD" refers to the limit of detection, defined as 2 standard deviations above the zero calibrator.

As used herein, the term "LLoQ" refers to the lower limit of quantification, defined from data generated off of the standard curve. Specifically, the back interpolated values of standards in triplicate provide CVs <20% and a bias <20% of the expected values.

As used herein, the terms "inflammatory disorder" and "inflammatory disease" refer to any of a number of conditions in which inflammation is increased over normal subjects. Non-limiting examples of inflammatory disorders are rheumatoid arthritis, Crohn's Disease, Inflammatory Bowel Disease, ulcerative colitis, psoriasis, and Chronic Obstructive Pulmonary Disease (COPD).

The American College of Rheumatology has developed criteria to aid in determining the progression, remission, and functional status of patients with RA.

Progression of RA (clinical and radiologic staging) is classified as follows: Stage 1 (early RA) is characterized by no destructive changes observed upon roentgenographic examination; radiographic evidence of osteoporosis is possible. Stage II (moderate progression) is characterized by radiographic evidence of periarticular osteoporosis, with or without slight subchondral bone destruction; slight cartilage destruction is possible; joint mobility is possibly limited; no joint deformities are observed; adjacent muscle atrophy is observed; extra-articular soft-tissue lesions (eg, nodules, tenosynovitis) are possible. Stage III (severe progression) is characterized by radiographic evidence of cartilage and bone destruction in addition to periarticular osteoporosis; joint deformity (e.g., subluxation, ulnar deviation, hyperextension) without fibrous or bony ankylosis; extensive muscle atrophy; and extra-articular soft-tissue lesions (eg, nodules, tenosynovitis) are possible. Stage IV (terminal progression) is characterized by fibrous or bony ankylosis in addition to the criteria of Stage III.

Remission of RA is defined as ≥5 of the following conditions occurring for at least 2 consecutive months: duration of morning stiffness does not exceed 15 minutes; no fatigue; no joint pain; no joint tenderness or pain with motion; no soft-tissue swelling in joints or tendon sheaths; ESR (erythrocyte sedimentation rate) of less than 30 millimeters/hour (mm/h) in a female or less than 20 mm/h in a male.

Functional status of patients with RA is defined as follows: Class I individuals are completely able to perform usual activities of daily living. Class II individuals are able to perform usual self-care and vocational activities but limited in avocational activities. Class III individuals are able to perform usual self-care activities but limited in vocational and avocational activities. Class IV individuals are limited in ability to perform usual self-care, vocational, and avocational activities.

We hypothesized that the concentrations of many cytokines and matrix metalloproteinases in blood serum or plasma may parallel the relative abundance in inflamed joints of RA patients, and that a highly sensitive assay could be used to measure them. Further, we hypothesized that differences in cytokine concentrations could be determined between RA patients and otherwise healthy matched controls with such highly sensitive assays. Herein we describe the use of a highly sensitive immunoassay system to measure cytokines and other biomarkers in blood plasma obtained from RA patients and healthy control subjects and describe differences in biomarker concentrations that we have discovered between these two study groups. The measurement of differences in the biomarker concentrations, either up- or down-regulated, singly or in combination, in RA patients versus control subjects provides opportunities for better (e.g., simpler, earlier, faster) disease diagnosis, disease staging, risk classification, and/or identification of therapy responders/non-responders.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F or IL-17F greater than healthy volunteer average concentrations for IL-17A, IL-17A/F or IL-17F, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentra or other inflammatory disorder tions for totMMP-9, the subject is predicted to have a greater than normal risk of developing RA.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F or IL-17F greater than healthy volunteer average concentrations for IL-17A, IL-17A/F or IL-17F, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, in combination with one or more of a concentration of IL-1β less than about 1.1 pg/ml, a concentration of IL-6 greater than about 1.0 pg/ml, or a concentration of totMMP-9 less than about 5.0 ng/ml, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, in combination with one or more of a concentration of IL-1β less than about 1.1 pg/ml, a concentration of IL-6 greater than about 1.0 pg/ml, or a concentration of totMMP-9 less than about 5.0 ng/ml, the subject is predicted to have a greater than normal risk of developing RA.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, in combination with a concentration of IL-1β less than about 1.1 pg/ml, a concentration of IL-6 greater than about 1.0 pg/ml, and a concentration of totMMP-9 less than about 5.0 ng/ml, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, in combination with a concentration of IL-1β less than about 1.1 pg/ml, a concentration of IL-6 greater than about 1.0 pg/ml, and a concentration of totMMP-9 less than about 5.0 ng/ml, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F or IL-17F greater than healthy volunteer average concentrations for IL-17A, IL-17A/F or IL-17F, in combination with one or more of a concentration of IL-1β less than about 1.1 pg/ml, a concentration of IL-6 greater than about 1.0 pg/ml, or a concentration of totMMP-9 less than about 5.0 ng/ml, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F or IL-17F greater than healthy volunteer average concentrations for IL-17A, IL-17A/F or IL-17F, in combination with a concentration of IL-1β less than about 1.1 pg/ml, a concentration of IL-6 greater than about 1.0 pg/ml, and a concentration of totMMP-9 less than about 5.0 ng/ml, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, in combination with one or more of a concentration of IL-1β less than about 1.1 pg/ml, a concentration of IL-6 greater than about 1.0 pg/ml, or a concentration of totMMP-9 less than about 5.0 ng/ml, the subject is predicted to have a greater than normal risk of developing RA or other inflammatory disorder.

In an aspect, the disclosure provides methods for predicting the risk for developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, in combination with a concentration of IL-1β less than about 1.1 pg/ml, a concentration of IL-6 greater than about 1.0 pg/ml, and a concentration of totMMP-9 less than about 5.0 ng/ml, the subject is predicted to have a greater than normal risk of developing RA or other inflammatory disorder.

For any of the above aspects related to predicting the risk for developing RA or other inflammatory disorder in a subject, the methods pertain to predicting the risk for developing RA.

For any of the above aspects related to predicting the risk for developing RA or other inflammatory disorder in a subject, the methods pertain to predicting the risk for developing Crohn's Disease.

For any of the above aspects related to predicting the risk for developing RA or other inflammatory disorder in a subject, the methods pertain to predicting the risk for developing Inflammatory Bowel Disease.

For any of the above aspects related to predicting the risk for developing RA or other inflammatory disorder in a subject, the methods pertain to predicting the risk for developing ulcerative colitis.

For any of the above aspects related to predicting the risk for developing RA or other inflammatory disorder in a subject, the methods pertain to predicting the risk for developing psoriasis.

For any of the above aspects related to predicting the risk for developing RA or other inflammatory disorder in a subject, the methods pertain to predicting the risk for developing Chronic Obstructive Pulmonary Disease (COPD).

In another aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F or IL-17F greater than healthy volunteer average concentrations for IL-17A, IL-17A/F or IL-17F, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F or IL-17F greater than healthy volunteer average concentrations for IL-17A, IL-17A/F or IL-17F, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, in combination with one or more of a concentration of IL-1β less than about 1.1 pg/ml, a concentration of IL-6 greater than about 1.0 pg/ml, or a concentration of totMMP-9 less than about 5.0 ng/ml, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, in combination with one or more of a concentration of IL-1β less than about 1.1 pg/ml, a concentration of IL-6 greater than about 1.0 pg/ml, or a concentration of totMMP-9 less than about 5.0 ng/ml, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml or of IL-17F of greater than about 116 pg/ml, in combination with a concentration of IL-1β less than about 1.1 pg/ml, a concentration of IL-6 greater than about 1.0 pg/ml, and a concentration of totMMP-9 less than about 5.0 ng/ml, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A greater than about 0.18 pg/ml, of IL-17A/F greater than about 1.35 pg/ml and of IL-17F of greater than about 116 pg/ml, in combination with a concentration of IL-1β less than about 1.1 pg/ml, a concentration of IL-6 greater than about 1.0 pg/ml, and a concentration of totMMP-9 less than about 5.0 ng/ml, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F or IL-17F greater than healthy volunteer average concentrations for IL-17A, IL-17A/F or IL-17F, in combination with one or more of a concentration of IL-1β less than about 1.1 pg/ml, a concentration of IL-6 greater than about 1.0 pg/ml, or a concentration of totMMP-9 less than about 5.0 ng/ml, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F or IL-17F greater than healthy volunteer average concentrations for IL-17A, IL-17A/F or IL-17F, in combination with a concentration of IL-1β less than about 1.1 pg/ml, a concentration of IL-6 greater than about 1.0 pg/ml, and a concentration of totMMP-9 less than about 5.0 ng/ml, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, in combination with one or more of a concentration of IL-1β less than about 1.1 pg/ml, a concentration of IL-6 greater than about 1.0 pg/ml, or a concentration of totMMP-9 less than about 5.0 ng/ml, the subject has an increased likelihood of developing RA or other inflammatory disorder.

In an aspect, the disclosure provides methods for determining the likelihood of developing RA or other inflammatory disorder in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the subject has a concentration of IL-17A, IL-17A/F and IL-17F greater than healthy volunteer average concentrations for IL-17A, IL-17A/F and IL-17F, in combination with a concentration of IL-1β less than about 1.1 pg/ml, a concentration of IL-6 greater than about 1.0 pg/ml, and a concentration of totMMP-9 less than about 5.0 ng/ml, the subject has an increased likelihood of developing RA or other inflammatory disorder.

For any of the above aspects related to determining the likelihood of developing RA or other inflammatory disorder in a subject, the methods pertain to determining the likelihood of developing RA.

For any of the above aspects related to determining the likelihood of developing RA or other inflammatory disorder in a subject, the methods pertain to determining the likelihood of developing Crohn's Disease.

For any of the above aspects related to determining the likelihood of developing RA or other inflammatory disorder in a subject, the methods pertain to determining the likelihood of developing Inflammatory Bowel Disease.

For any of the above aspects related to determining the likelihood of developing RA or other inflammatory disorder in a subject, the methods pertain to determining the likelihood of developing ulcerative colitis.

For any of the above aspects related to determining the likelihood of developing RA or other inflammatory disorder in a subject, the methods pertain to determining the likelihood of developing psoriasis.

For any of the above aspects related to determining the likelihood of developing RA or other inflammatory disorder in a subject, the methods pertain to determining the likelihood of developing Chronic Obstructive Pulmonary Disease (COPD).

Figure 3:
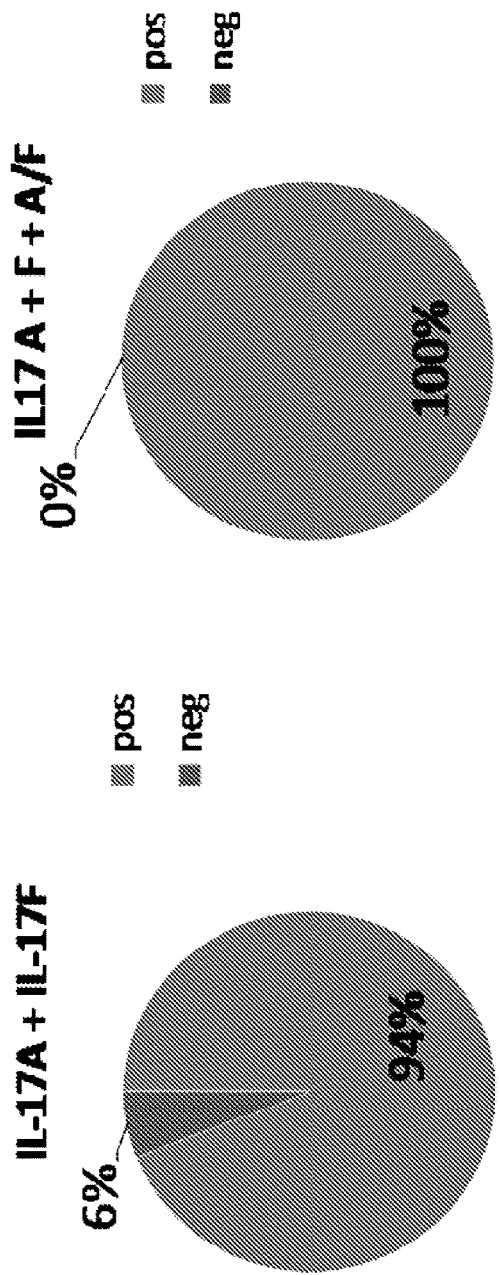
FIG. 3 illustrates the heretofore unknown importance of the IL-17A, IL-17F, IL-17A/F heterodimer in RA biology. Only 6% of RA patients in the sample had neither IL-17A nor IL-17F present at elevated concentrations over HV. All RA patients had at least one of IL-17A, IL-17F, and IL-17A/F heterodimer present at elevated concentrations over HV.
Figure 4A:
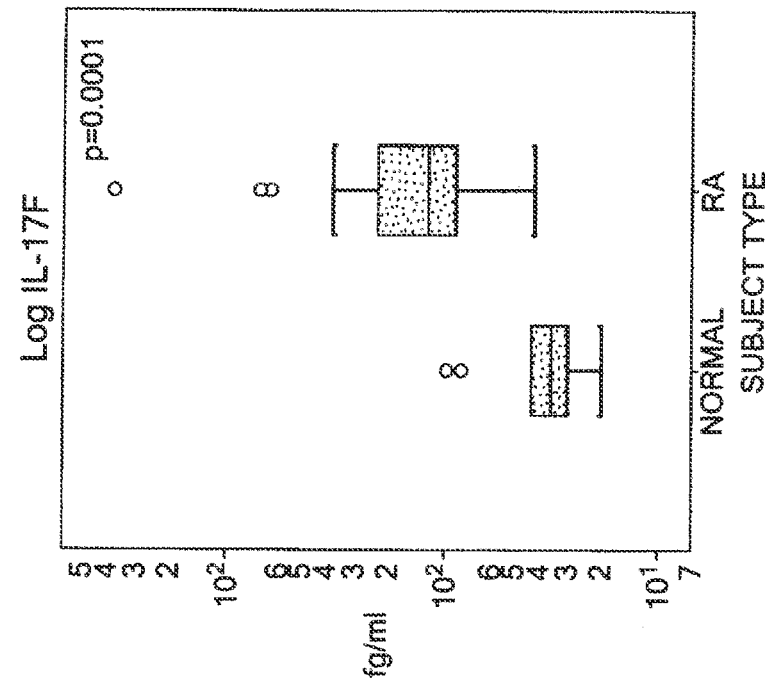
FIGS. 4A-4F show box plots of the markers that best classify RA along with a box plot for TNFα.
Figure 4B:
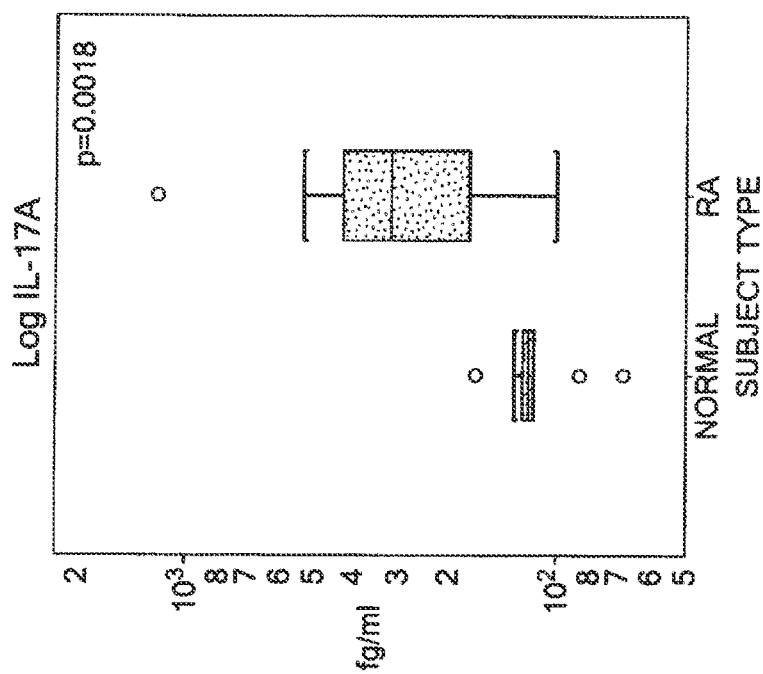
Figure 4D:
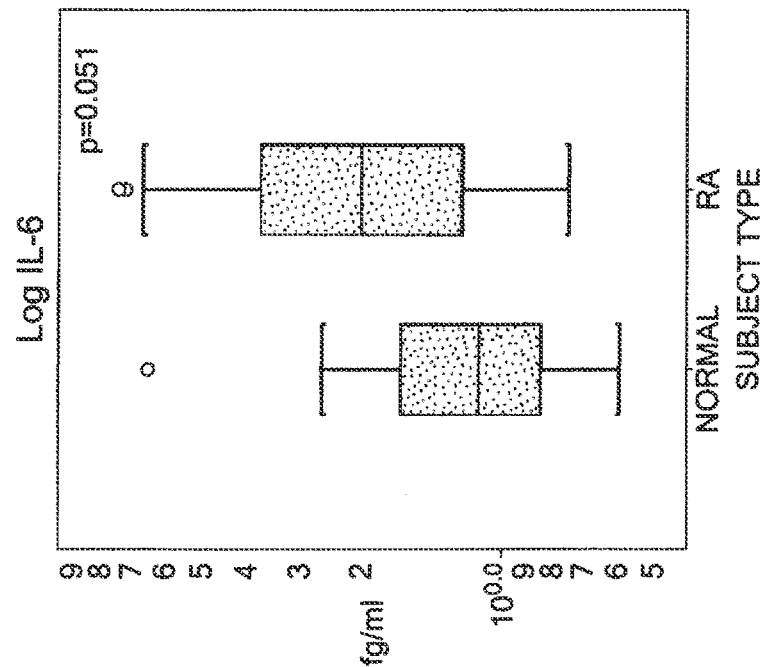
Figure 4C:
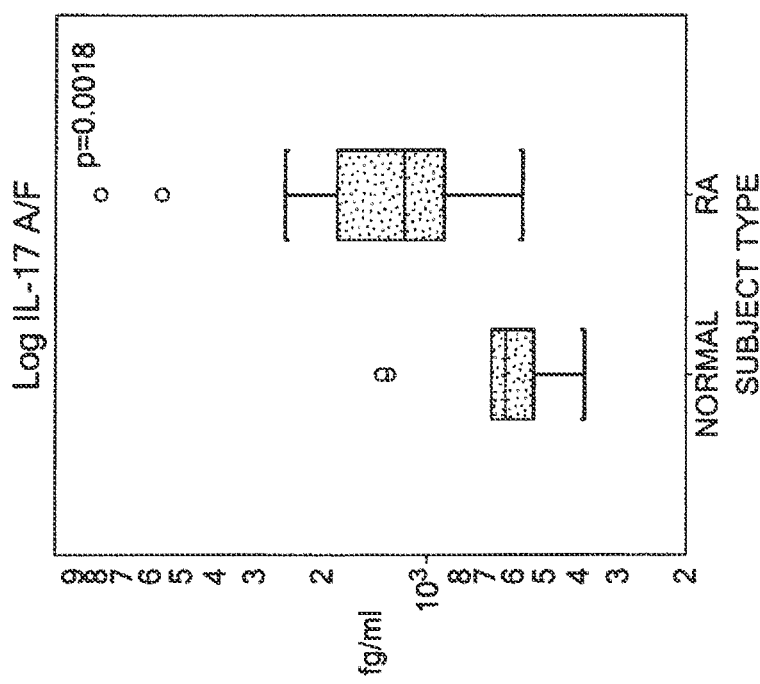
Figure 4E:
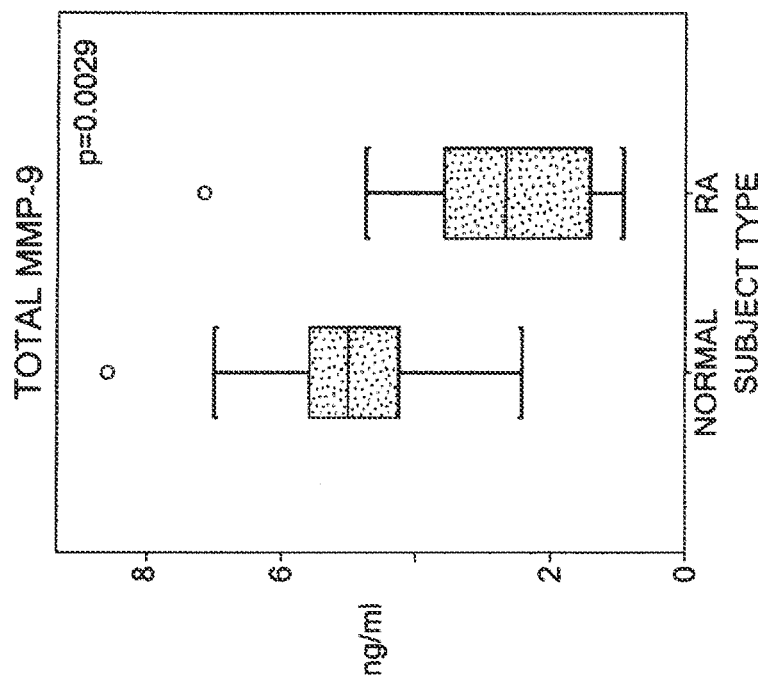
Figure 4F:
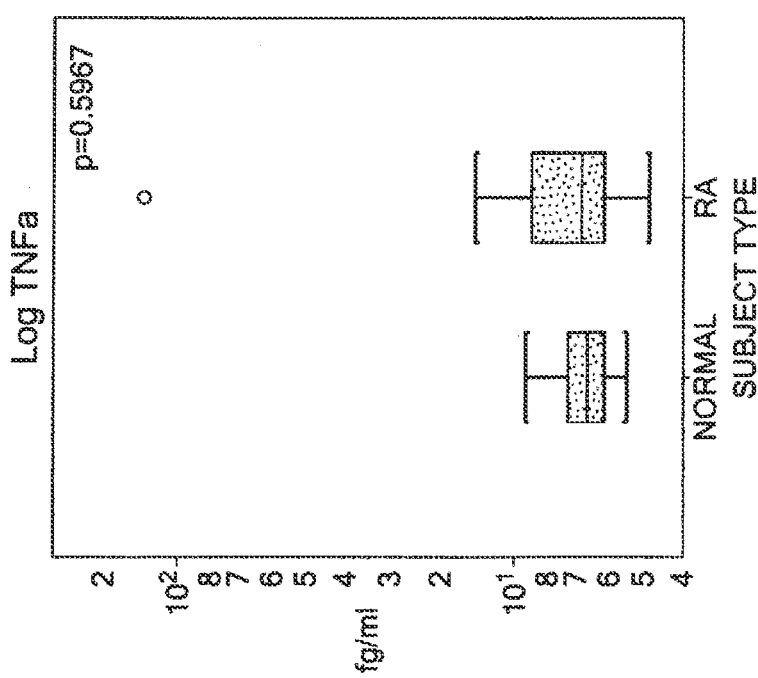
Figure 6:
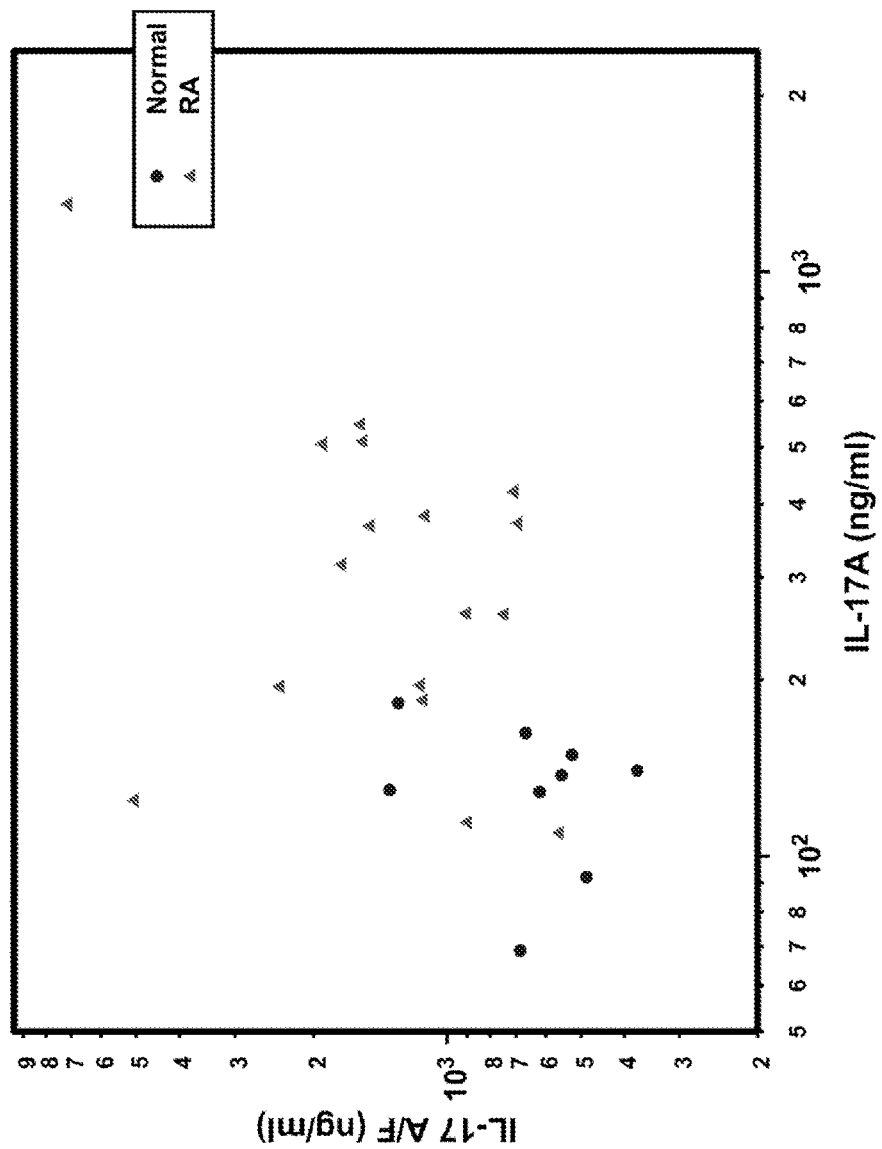
FIG. 6 shows that the combination of IL-17A and IL-17 A/F as biomarkers for RA perform very well in predicting disease.
Figure 7:
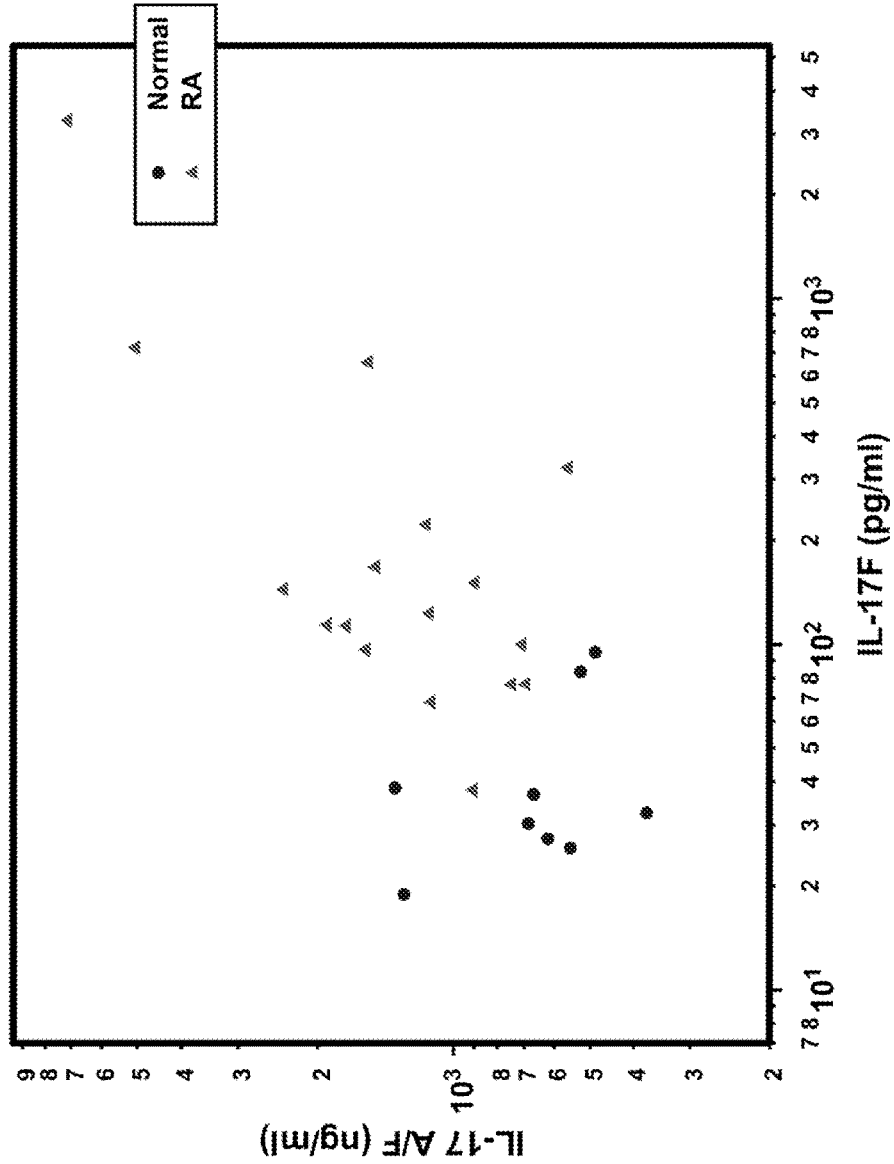
FIG. 7 shows that the combination of IL-17F and IL-17 A/F as biomarkers for RA perform very well in predicting disease.

In another aspect, the disclosure provides methods for determining inflammatory disease in a patient. For example a number of markers can be used to diagnose existing inflammatory disease such as RA. FIGS. 1, 2, and 3 show the that patients with elevated levels of IL-17A, IL-17F, and IL-17A/F, either alone or in combination, are likely to be suffering from RA. Other markers, such as IL-1β, IL-6, totMMP-9, proMMP-9, and cTnI, are also useful in determining disease. Accordingly, in on aspect the disclosure is provides a method of detecting inflammatory disease by measuring the amount of one or more of IL-17A, IL-17F, IL-17A/F, IL-1β, IL-6, totMMP-9, proMMP-9, and cTnI, in a patient sample, comparing the sample to a control population, and determining whether a patient is suffering from inflammatory disease. Statistically significant differences between the patient sample and the control population (healthy volunteers) for one or more markers can be indicative of disease. As shown in FIG. 3, only 6% of RA patients in the reference population had neither IL-17A nor IL-17F present at elevated concentrations over healthy volunteers (HV). All RA patients had at least one of IL-17A, IL-17F, and IL-17A/F heterodimer present at elevated concentrations over (HV). In particular embodiments, as shown in FIGS. 5, 6 and 7, the combination of IL-17F & IL-17A, the combination of IL-17A and IL-17 A/F, or the combination of IL-17F and IL-17 A/F can be used as biomarkers in diagnosing RA.

In another aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the patient has a first concentration of IL-17A greater than about 0.18 pg/ml, of IL-17A/F greater than about 1.35 pg/ml or of IL-17F of greater than about 116 pg/ml, and a second concentration of IL-17A less than about 0.18 pg/ml, of IL-17A/F less than about 1.35 pg/ml or of IL-17F of less than about 116 pg/ml, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A greater than about 0.18 pg/ml, of IL-17A/F greater than about 1.35 pg/ml and of IL-17F of greater than about 116 pg/ml, and a second concentration of IL-17A less than about 0.18 pg/ml, of IL-17A/F less than about 1.35 pg/ml and of IL-17F of less than about 116 pg/ml, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A greater than about 0.18 pg/ml, of IL-17A/F greater than about 1.35 pg/ml or of IL-17F of greater than about 116 pg/ml, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, and a second concentration of IL-17A less than about 0.18 pg/ml, of IL-17A/F less than about 1.35 pg/ml or of IL-17F of less than about 116 pg/ml, in combination with one or more of a concentration of IL-1β substantially the same as healthy volunteer average concentrations for IL-1β, a concentration of IL-6 substantially the same as healthy volunteer average concentrations for IL-6, or a concentration of totMMP-9 substantially the same as healthy volunteer average concentrations for totMMP-9, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A greater than about 0.18 pg/ml, of IL-17A/F greater than about 1.35 pg/ml and of IL-17F of greater than about 116 pg/ml, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, and a second concentration of IL-17A less than about 0.18 pg/ml, of IL-17A/F less than about 1.35 pg/ml and of IL-17F of less than about 116 pg/ml, in combination with one or more of a concentration of IL-1β substantially the same as healthy volunteer average concentrations for IL-1β, a concentration of IL-6 substantially the same as healthy volunteer average concentrations for IL-6, or a concentration of totMMP-9 substantially the same as healthy volunteer average concentrations for totMMP-9, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A greater than about 0.18 pg/ml, of IL-17A/F greater than about 1.35 pg/ml or of IL-17F of greater than about 116 pg/ml, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, and a second concentration of IL-17A less than about 0.18 pg/ml, of IL-17A/F less than about 1.35 pg/ml or of IL-17F of less than about 116 pg/ml, in combination with a concentration of IL-1β substantially the same as healthy volunteer average concentrations for IL-1β, a concentration of IL-6 substantially the same as healthy volunteer average concentrations for IL-6, and a concentration of totMMP-9 substantially the same as healthy volunteer average concentrations for totMMP-9, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A greater than about 0.18 pg/ml, of IL-17A/F greater than about 1.35 pg/ml and of IL-17F of greater than about 116 pg/ml, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, and a second concentration of IL-17A less than about 0.18 pg/ml, of IL-17A/F less than about 1.35 pg/ml or of IL-17F of less than about 116 pg/ml, in combination with a concentration of IL-1β substantially the same as healthy volunteer average concentrations for IL-1β, a concentration of IL-6 substantially the same as healthy volunteer average concentrations for IL-6, and a concentration of totMMP-9 substantially the same as healthy volunteer average concentrations for totMMP-9, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F or IL-17F greater than healthy volunteer average concentrations for IL-17A, IL-17A/F or IL-17F, and a second concentration of one or more of IL-17A, IL-17A/F or IL-17F substantially the same as healthy volunteer concentrations for IL-17A, IL-17A/F or IL-17F, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F and IL-17F greater than healthy volunteer average concentrations for IL-17A, IL-17A/F and IL-17F, and a second concentration of IL-17A, IL-17A/F and IL-17F substantially the same as healthy volunteer concentrations for IL-17A, IL-17A/F and IL-17F, the RA or other inflammatory disorder patient is identified as a patient who responds to therapy.

In an aspect, the disclosure provides methods for identifying RA or other an inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F or IL-17F greater than healthy volunteer average concentrations for IL-17A, IL-17A/F or IL-17F, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, and a second concentration of IL-17A, IL-17A/F or IL-17F substantially the same as healthy volunteer concentrations for IL-17A, IL-17A/F or IL-17F, in combination with one or more of a concentration of IL-1β substantially the same as healthy volunteer average concentrations for IL-1β, a concentration of IL-6 substantially the same as healthy volunteer average concentrations for IL-6, or a concentration of totMMP-9 substantially the same as healthy volunteer average concentrations for totMMP-9, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F or IL-17F greater than healthy volunteer average concentrations for IL-17A, IL-17A/F and IL-17F, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, and a second concentration of IL-17A, IL-17A/F or IL-17F substantially the same as healthy volunteer concentrations for IL-17A, IL-17A/F or IL-17F, in combination with a concentration of IL-1β substantially the same as healthy volunteer average concentrations for IL-1β, a concentration of IL-6 substantially the same as healthy volunteer average concentrations for IL-6, and a concentration of totMMP-9 substantially the same as healthy volunteer average concentrations for totMMP-9, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F and IL-17F greater than healthy volunteer average concentrations for IL-17A, IL-17A/F and IL-17F, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, and a second concentration of IL-17A, IL-17A/F and IL-17F substantially the same as healthy volunteer concentrations for IL-17A, IL-17A/F and IL-17F, in combination with one or more of a concentration of IL-1β substantially the same as healthy volunteer average concentrations for IL-1β, a concentration of IL-6 substantially the same as healthy volunteer average concentrations for IL-6, or a concentration of totMMP-9 substantially the same as healthy volunteer average concentrations for totMMP-9, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F and IL-17F greater than healthy volunteer average concentrations for IL-17A, IL-17A/F and IL-17F, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, and a second concentration of IL-17A, IL-17A/F and IL-17F substantially the same as healthy volunteer concentrations for IL-17A, IL-17A/F and IL-17F, in combination with a concentration of IL-1β substantially the same as healthy volunteer average concentrations for IL-1β, a concentration of IL-6 substantially the same as healthy volunteer average concentrations for IL-6, and a concentration of totMMP-9 substantially the same as healthy volunteer average concentrations for totMMP-9, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A greater than about 0.18 pg/ml, of IL-17A/F greater than about 1.35 pg/ml or of IL-17F of greater than about 116 pg/ml, in combination with one or more of a concentration of IL-1β less than about 1.1 pg/ml, a concentration of IL-6 greater than about 1.0 pg/ml, or a concentration of totMMP-9 less than about 5.0 ng/ml, and a second concentration of IL-17A less than about 0.18 pg/ml, of IL-17A/F less than about 1.35 pg/ml or of IL-17F of less than about 116 pg/ml, in combination with one or more of a concentration of IL-1β greater than about 1.1 pg/ml, a concentration of IL-6 less than about 1.0 pg/ml, or a concentration of totMMP-9 greater than about 5.0 ng/ml, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A greater than about 0.18 pg/ml, of IL-17A/F greater than about 1.35 pg/ml and of IL-17F of greater than about 116 pg/ml, in combination with one or more of a concentration of IL-1β less than about 1.1 pg/ml, a concentration of IL-6 greater than about 1.0 pg/ml, or a concentration of totMMP-9 less than about 5.0 ng/ml, and a second concentration of IL-17A less than about 0.18 pg/ml, of IL-17A/F less than about 1.35 pg/ml or of IL-17F of less than about 116 pg/ml, in combination with one or more of a concentration of IL-1β greater than about 1.1 pg/ml, a concentration of IL-6 less than about 1.0 pg/ml, or a concentration of totMMP-9 greater than about 5.0 ng/ml, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A greater than about 0.18 pg/ml, of IL-17A/F greater than about 1.35 pg/ml or of IL-17F of greater than about 116 pg/ml, in combination with a concentration of IL-1β less than about 1.1 pg/ml, a concentration of IL-6 greater than about 1.0 pg/ml, and a concentration of totMMP-9 less than about 5.0 ng/ml, and a second concentration of IL-17A less than about 0.18 pg/ml, of IL-17A/F less than about 1.35 pg/ml or of IL-17F of less than about 116 pg/ml, in combination with a concentration of IL-1β greater than about 1.1 pg/ml, a concentration of IL-6 less than about 1.0 pg/ml, and a concentration of totMMP-9 greater than about 5.0 ng/ml, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A greater than about 0.18 pg/ml, of IL-17A/F greater than about 1.35 pg/ml and of IL-17F of greater than about 116 pg/ml, in combination with a concentration of IL-1β less than about 1.1 pg/ml, a concentration of IL-6 greater than about 1.0 pg/ml, and a concentration of totMMP-9 less than about 5.0 ng/ml, and a second concentration of IL-17A less than about 0.18 pg/ml, of IL-17A/F less than about 1.35 pg/ml and of IL-17F of less than about 116 pg/ml, in combination with a concentration of IL-1β greater than about 1.1 pg/ml, a concentration of IL-6 less than about 1.0 pg/ml, and a concentration of totMMP-9 greater than about 5.0 ng/ml, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F or IL-17F greater than healthy volunteer average concentrations for IL-17A, IL-17A/F or IL-17F, in combination with one or more of a concentration of IL-1β less than about 1.1 pg/ml, a concentration of IL-6 greater than about 1.0 pg/ml, or a concentration of totMMP-9 less than about 5.0 ng/ml, and a second concentration of IL-17A, IL-17A/F or IL-17F substantially the same as healthy volunteer concentrations for IL-17A, IL-17A/F or IL-17F, in combination with one or more of a concentration of IL-1β greater than about 1.1 pg/ml, a concentration of IL-6 less than about 1.0 pg/ml, and a concentration of totMMP-9 greater than about 5.0 ng/ml, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F or IL-17F greater than healthy volunteer average concentrations for IL-17A, IL-17A/F or IL-17F, in combination with a concentration of IL-1β less than about 1.1 pg/ml, a concentration of IL-6 greater than about 1.0 pg/ml, and a concentration of totMMP-9 less than about 5.0 ng/ml, and a second concentration of IL-17A, IL-17A/F or IL-17F substantially the same as healthy volunteer concentrations for IL-17A, IL-17A/F or IL-17F, in combination with a concentration of IL-1β greater than about 1.1 pg/ml, a concentration of IL-6 less than about 1.0 pg/ml, and a concentration of totMMP-9 greater than about 5.0 ng/ml, the RA or other inflammatory disorder patient is identified as a patient who responds to therapy.

In an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F and IL-17F greater than healthy volunteer average concentrations for IL-17A, IL-17A/F and IL-17F, in combination with one or more of a concentration of IL-1β less than about 1.1 pg/ml, a concentration of IL-6 greater than about 1.0 pg/ml, or a concentration of totMMP-9 less than about 5.0 ng/ml, and a second concentration of IL-17A, IL-17A/F and IL-17F substantially the same as healthy volunteer concentrations for IL-17A, IL-17A/F and IL-17F, in combination with one or more of a concentration of IL-1β greater than about 1.1 pg/ml, a concentration of IL-6 less than about 1.0 pg/ml, and a concentration of totMMP-9 greater than about 5.0 ng/ml, the RA or other inflammatory disorder patient is identified as a patient who responds to therapy.

an aspect, the disclosure provides methods for identifying an RA or other inflammatory disorder patient who responds to therapy, comprising obtaining a first sample from the patient, determining a first concentration of each of IL-17A, IL-17A/F, and IL-17F, and optionally one or more of IL-1β, IL-6, totMMP-9, proMMP-9, cTnI, and combinations thereof in the first sample, administering a therapy to the patient, obtaining a second sample from the patient, and determining a second concentration of each of IL-17A, IL-17A/F, and IL-17F, and optionally one or more of IL-1β, IL-6, totMMP-9, proMMP-9, cTnI, and combinations thereof in the second sample, wherein when the subject has a first concentration of IL-17A, IL-17A/F and IL-17F greater than healthy volunteer average concentrations for IL-17A, IL-17A/F and IL-17F, in combination with a concentration of IL-1β less than about 1.1 pg/ml, a concentration of IL-6 greater than about 1.0 pg/ml, and a concentration of totMMP-9 less than about 5.0 ng/ml, and a second concentration of IL-17A, IL-17A/F and IL-17F substantially the same as healthy volunteer concentrations for IL-17A, IL-17A/F and IL-17F, in combination with a concentration of IL-1β greater than about 1.1 pg/ml, a concentration of IL-6 less than about 1.0 pg/ml, and a concentration of totMMP-9 greater than about 5.0 ng/ml, the RA or other inflammatory disorder patient is identified as a patient who responds to therapy.

For any of the above aspects related to identifying an RA or other inflammatory disorder patient who responds to therapy, the methods pertain to identifying an RA patient who responds to therapy.

For any of the above aspects related to identifying an RA or other inflammatory disorder patient who responds to therapy, the methods pertain to identifying a Crohn's Disease patient who responds to therapy.

For any of the above aspects related to identifying an RA or other inflammatory disorder patient who responds to therapy, the methods pertain to identifying a Inflammatory Bowel Disease patient who responds to therapy.

For any of the above aspects related to identifying an RA or other inflammatory disorder patient who responds to therapy, the methods pertain to identifying an ulcerative colitis patient who responds to therapy.

For any of the above aspects related to identifying an RA or other inflammatory disorder patient who responds to therapy, the methods pertain to identifying a psoriasis patient who responds to therapy.

For any of the above aspects related to identifying an RA or other inflammatory disorder patient who responds to therapy, the methods pertain to identifying a COPD patient who responds to therapy.

In another aspect, the disclosure provides methods for predicting the rate of inflammatory disease progression in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the concentration of none or one of IL-17A is greater than 0.18 pg/ml, IL-17-F is greater than 116 pg/ml, or IL-17A/F is greater than 1.35 pg/ml, and wherein when the concentration of one of IL-1β is less than 1.1. pg/ml, totMMP-9 is less than 5.0 ng/ml, or IL-6 is greater than 1.0 pg/ml, the subject is predicted to have a slow rate of inflammatory disease progression.

In an aspect, the disclosure provides methods for predicting the rate of inflammatory disease progression, wherein when the concentrations of one of IL-17A is greater than 0.18 pg/ml, the concentration of IL-17-F is greater than 116 pg/ml, and the concentration of IL-17A/F is greater than 1.35 pg/ml, and wherein when the concentration of one or more of IL-1β is less than 1.1. pg/ml, totMMP-9 is less than 5.0 ng/ml, and IL-6 is greater than 1.0 pg/ml, the subject is predicted to have a medium rate of inflammatory disease progression.

In an aspect, the disclosure provides methods for predicting the rate of inflammatory disease progression, wherein when the concentrations of one or more of IL-17A is greater than 0.18 pg/ml, the concentration of IL-17-F is greater than 116 pg/ml, and the concentration of IL-17A/F is greater than 1.35 pg/ml, and wherein when the concentration of at least two of IL-1β is less than 1.1. pg/ml, totMMP-9 is less than 5.0 ng/ml, and IL-6 is greater than 1.0 pg/ml, the subject is predicted to have a high rate of inflammatory disease progression.

In another aspect, the disclosure provides methods for predicting the likelihood of inflammatory disease remission in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the concentration of none or one of IL-17A is greater than 0.18 pg/ml, IL-17-F is greater than 116 pg/ml, or IL-17A/F is greater than 1.35 pg/ml, and wherein when the concentration of one of IL-1β is less than 1.1. pg/ml, totMMP-9 is less than 5.0 ng/ml, or IL-6 is greater than 1.0 pg/ml, the subject is predicted to have a high likelihood of inflammatory disease remission.

In an aspect, the disclosure provides methods for predicting the likelihood of inflammatory disease remission in a subject, wherein when the concentrations of one of IL-17A is greater than 0.18 pg/ml, the concentration of IL-17-F is greater than 116 pg/ml, and the concentration of IL-17A/F is greater than 1.35 pg/ml, and wherein when the concentration of one or more of IL-1β is less than 1.1. pg/ml, totMMP-9 is less than 5.0 ng/ml, and IL-6 is greater than 1.0 pg/ml, the subject is predicted to have a medium likelihood of inflammatory disease remission.

In an aspect, the disclosure provides methods for predicting the likelihood of inflammatory disease remission in a subject, wherein when the concentrations of one or more of IL-17A is greater than 0.18 pg/ml, the concentration of IL-17-F is greater than 116 pg/ml, and the concentration of IL-17A/F is greater than 1.35 pg/ml, and wherein when the concentration of at least two of IL-1β is less than 1.1. pg/ml, totMMP-9 is less than 5.0 ng/ml, and IL-6 is greater than 1.0 pg/ml, the subject is predicted to have a low likelihood of inflammatory disease remission.

In another aspect, the disclosure provides methods for determining the severity of inflammatory disease in a subject, comprising obtaining a sample from the subject, determining a concentration of each of IL-17A, IL-17A/F, and IL-17F, and optionally one or more of IL-1β, IL-6, totMMP-9, proMMP-9, cTnI, and combinations thereof in the sample, wherein when the concentration of one of IL-17A is greater than 0.18 pg/ml, IL-17-F is greater than 116 pg/ml, or IL-17A/F is greater than 1.35 pg/ml, and wherein when the concentration of none or one of IL-1β is less than 1.1. pg/ml, totMMP-9 is less than 5.0 ng/ml, or IL-6 is greater than 1.0 pg/ml, the subject is determined to have mild inflammatory disease.

In an aspect, the disclosure provides methods for determining the severity of inflammatory disease in a subject, wherein when the concentrations of at least one of IL-17A is greater than 0.18 pg/ml, the concentration of IL-17-F is greater than 116 pg/ml, or the concentration of IL-17A/F is greater than 1.35 pg/ml, and wherein when the concentration of one or more of IL-1β is less than 1.1. pg/ml, totMMP-9 is less than 5.0 ng/ml, and IL-6 is greater than 1.0 pg/ml, the subject is determined to have moderate inflammatory disease.

In another aspect, the disclosure provides methods for determining the severity of inflammatory disease in a subject, wherein when the concentrations of at least one of IL-17A is greater than 0.18 pg/ml, the concentration of IL-17-F is greater than 116 pg/ml, and the concentration of IL-17A/F is greater than 1.35 pg/ml, and wherein when the concentration of two or more of IL-1β is less than 1.1. pg/ml, totMMP-9 is less than 5.0 ng/ml, and IL-6 is greater than 1.0 pg/ml, the subject is determined to have severe inflammatory disease.

For any of the above aspects related to predicting the rate of inflammatory disease progression, predicting the likelihood of inflammatory disease remission, or determining the severity of inflammatory disease, the inflammatory disease is RA, Crohn's Disease, IBD, ulcerative colitis, psoriasis, or COPD.

For any of the above aspects related to predicting the rate of inflammatory disease progression, predicting the likelihood of inflammatory disease remission, or determining the severity of inflammatory disease, the inflammatory disease is RA.

For any of the above aspects related to predicting the rate of inflammatory disease progression, predicting the likelihood of inflammatory disease remission, or determining the severity of inflammatory disease, the inflammatory disease is Crohn's Disease.

For any of the above aspects related to predicting the rate of inflammatory disease progression, predicting the likelihood of inflammatory disease remission, or determining the severity of inflammatory disease, the inflammatory disease is IBD.

For any of the above aspects related to predicting the rate of inflammatory disease progression, predicting the likelihood of inflammatory disease remission, or determining the severity of inflammatory disease, the inflammatory disease is ulcerative colitis.

For any of the above aspects related to predicting the rate of inflammatory disease progression, predicting the likelihood of inflammatory disease remission, or determining the severity of inflammatory disease, the inflammatory disease is psoriasis.

For any of the above aspects related to predicting the rate of inflammatory disease progression, predicting the likelihood of inflammatory disease remission, or determining the severity of inflammatory disease, the inflammatory disease is COPD.

In various embodiments of the methods disclosed herein, concentrations of biomarkers related to RA or other inflammatory disorder comprise values that are elevated or reduced relative to the concentrations of those same biomarkers in a normal population of subjects (e.g., the HV group as provided herein). One of skill in the art may also measure biomarker concentrations in one or more HV populations utilizing an apparatus capable of sensitively measuring the concentrations of biomarkers described herein and calculate the average values for each biomarker in such HV populations.

In embodiments of the methods, the sample can be a single sample from the subject. In some embodiments, the sample can be a series of samples taken at various points in time so that changes in concentration over time of biomarker related to RA or other inflammatory disorder can be identified and interpreted. In embodiments, the samples can be taken in over the course of hours, days, weeks, months, and years. The samples can be taken at any regular or irregular interval based on the detected concentration(s) of biomarker related to RA or other inflammatory disorder and/or the change in the concentration(s) of biomarker related to RA or other inflammatory disorder in the one or more samples over time.

In embodiments that track patient data and samples over time, such information can be taken from any known clinical study or database that maintains such patient samples and/or patient history.

Systems for Detection

As noted above, the diagnostic/prognostic methods described herein generally involve the determination of the amount of biomarker related to RA or other inflammatory disorder from one or a set of samples from a subject. Determination of concentrations of biomarker related to RA or other inflammatory disorder in the practice of the methods can be performed using any suitable apparatus or system that allow for the detection levels described herein. Such suitable apparatus, includes, but is not limited to, the systems described in Published U.S. Patent Application Nos: 2009/0159812 (Livingston); 2008/0003685 (Goix, et al.); and U.S. Pat. No. 7,572,640, all incorporated herein by reference. U.S. Pat. No. 7,572,640 describes instruments, reagents and methods for measuring analytes at levels to carry out this invention and thus identify those patients with of biomarker related to RA levels above or below the normal HV range. As one example of a an analyzer suitable for the analysis of samples according to the methods described herein, US2009/0159812 describes an analyzer that uses digital analysis of single molecule count for determining the amount of analytes in sample. According to one embodiment of US2009/0159812, a sample in a sample well is scanned using an electromagnetic radiation source by translating an interrogation space through a sample. The sample is scanned at a speed that is sufficiently slow so that individually-labeled antibodies are measured during the sample scan. This is achieved by setting the interrogation space such that the emission of only one fluorescent molecule, if present, is detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of detected events/sample.

A feature that contributes to the extremely high sensitivity of the instruments and methods for detecting IL-17A, IL17A/F and IL17/F is the method of detecting and counting labels, which, in some embodiments, are attached to single molecules of IL-17A, IL17A/F and IL17/F to be detected or, more typically, correspond to a single molecule to be detected. Briefly, the sample contained in the sample plate is effectively divided into a series of detection events, by translating an interrogation space through the sample plate wherein electromagnetic radiation from a laser of an appropriate excitation wavelength for the fluorescent moiety used in the label for a predetermined period of time is directed to the wavelength, and photons emitted during that time are detected. Each predetermined period of time is a "bin." If the total number of photons detected in a given bin exceeds a predetermined threshold level, a detection event is registered for that bin, i.e., a label has been detected. If the total number of photons is not at the predetermined threshold level, no detection event is registered. In some embodiments, the processing sample concentration is dilute enough that, for a large percentage of detection events, the detection event represents only one label passing through the window, which corresponds to a single molecule of interest in the original sample. Accordingly, few detection events represent more than one label in a single bin. In some embodiments, further refinements are applied to allow greater concentrations of label in the processing sample to be detected accurately, i.e., concentrations at which the probability of two or more labels being detected as a single detection event is no longer insignificant.

Many bin measurements are taken to determine the concentration of a sample, and the absence or presence of a label is ascertained for each bin measurement. Typically, 60,000 measurements or more can be made in 1 min. 60,000 measurements are made in 1 minute when the bin size is 1 millisecond. For smaller bin sizes the number of measurements is correspondingly larger, e.g., 6,000,000 measurements per minute equates to a bin size of 10 microseconds. Because so many measurements are taken, no single measurement is crucial, thus providing for a high margin of error. Bins that are determined not to contain a label ("no" bins) are discounted and only the measurements made in the bins that are determined to contain label ("yes" bins) are accounted in determining the concentration of the label in the processing sample. Discounting measurements made in the "no" bins or bins that are devoid of label increases the signal to noise ratio and the accuracy of the measurements. Thus, in some embodiments, determining the concentration of a label in a sample comprises detecting the bin measurements that reflect the presence of a label.

To determine the concentration of labels in the processing sample, the total number of labels contained in the "yes" bins is determined relative to the sample volume represented by the total number of bins. Thus, in one embodiment, determining the concentration of a label in a processing sample comprises determining the total number of labels detected "yes" and relating the total number of detected labels to the total sample volume that was analyzed. The total sample volume that is analyzed is the sample volume through which the interrogation space is translated in a specified time interval. Alternatively, the concentration of the label complex in a sample is determined by interpolation of the signal emitted by the label in a number of bins from a standard curve that is generated by determining the signal emitted by labels in the same number of bins by standard samples containing known concentrations of the label.

In some embodiments, the number of individual labels detected in a bin is related to the relative concentration of the analyte in the processing sample. At relatively low concentrations, e.g., at concentrations below about $10^{-16}$ M, the number of labels is proportional to the photon signal detected in a bin. Thus, at low concentrations of label the photon signal is provided as a digital signal. With each signal representing a digital event, this configuration enables extremely high analytical sensitivities. Total fluorescent signal is determined as a sum of the individual digital events. Each molecule counted is a positive data point with hundreds to thousands of detected events/sample.

EXAMPLES

Example 1

The Erenna System, based upon Singulex Single Molecule Counting technology, was used for immunoassay analysis. This system has been described previously (Todd et al., Clin Chem. 53(11): 1990-1995 (2007); Todd et al., Clin Chem. 55(1):196-8 (2009); incorporated by reference). Immunoassays for the analytes described in the table below were constructed from commercially available antibodies and analytes. The immunoassay procedure used in the analyses of these analytes has been described previously as well (Todd et al., supra). All antibodies and analytes were obtained from R&D Systems (Minneapolis, Minn.) except for cTnI analyte, which was obtained from HyTest (Turku, Finland), and antibodies to cTnI, which were obtained from BiosPacific (Emeryville, Calif.). The volume of sample stated in Table 6 was added to a well in a 96 well plate, along with sufficient volume of calibrator diluent (3% BSA, Tris pH 8.0, 150 mM NaCl) to create a final volume of 100 ul for all test but for cTnI, which had a final volume of 50 ul. 100 ul of paramagnetic microparticles, and 150 ul for cTnI assays (MPs, MyOne, Invitrogen Dynal AS; approximately 5-10 ug MPs/well), coated with the capture antibody and diluted in assay buffer (1% BSA, Tris-buffered saline, pH 7.4, with 0.5 mL Triton X-100/L, and heterophile/human antimouse antibody-blocking reagents (from Scantibodies Laboratories, used per the manufacturer's recommendations)), were added to each well and incubated for about 2 hours (about 1 hour for cTnI and IL-1β). MPs were separated using a magnetic bed (Ambion). Supernatant was removed, MPs were washed once, and then 20 uL detection antibody (50-500 mg/L diluted in assay buffer) was added and incubated for about 1 hour at 25° C. with shaking. The MPs were again magnetically separated and washed 5 times using Tris-buffered saline with 0.5 mL Triton X-100/L. After removal of residual wash buffer, 20 uL elution buffer (Glycine pH 2.5) was added. This reagent disrupted antibody-analyte interactions and resulted in the release of detection antibody from the MPs. The solution in each 96-well plate was then transferred to a 384-well filter plate (0.2 um, AcroPrep cat. no. 5070, Pall) and centrifuged at 1200 g for 3 minutes to separate detection antibody in elution buffer from MPs. The eluted and filtered material in the 384-well plate was then placed into the Erenna Immunoassay System. The concentration of biomarker in each sample was determined via interpolation off a standard curve run with the samples. For samples that used a volume less than 100 ul, the resulting interpolated values were adjusted and standardized to a final sample volume of 100 ul (and 50 ul for cTnI). The value used to convert the standard into pg/mL was provided by the vendor.

All human serum specimens used in this study were obtained from ProMedDx (Norton, Mass.), and obtained under IRB approval and informed consent. All specimens were collected under protocol, which included noting time of blood collection into serum tubes, separation of serum from cells and storing of resulting serum at −70 C. Healthy volunteers (HV) refers to serum collected from otherwise healthy subjects, age range of 42-73 years. Rheumatoid arthritis (RA) refers to serum collected from 17 clinically documented RA patients that had an average rheumatoid factor (RF) value of 75 IU/mL. Approximately 50% of the RA patients were on TNF-a inhibitors. The age range for these subjects was 42-80. 59% were males and 41% were females. Matched controls refers to subjects that were matched in age and sex to the RA subjects, but did not have RA.

Using highly sensitive immunoassays we were able to quantify the concentration of a variety of analytes in serum obtained from HV, RA subjects and matched controls (FIGS. 1, 2). The analytes described in Table 1 and Table 2 were measureable in all study subjects. Importantly, all of the assays had limits of quantification (CV <20%) that were lower than the concentration of the analytes measured in serum. This ensured that the measurement of analyte was accurate. We made the following observations:

Cardiac Troponin-I (cTnI) was elevated in a number of RA patients. Of note the elevations were modest (average approx 11 pg/mL) which was 3-4 fold higher than the average value found in the matched controls (approximately 3 pg/mL). 15/16 of these RA patients had cTnI concentrations <approximately 50 pg/mL, which is the limit of quantification for commercially available cTnI assays. Thus, this small increase (but significant in terms of exceeding the 99% normal range (at CV <10%) of cTnI of 7 pg/ml) in cTnI could not be noted with other assays.

IL-17F was elevated in RA patients compared to matched controls. This is the first time that anyone has found IL-17F to be elevated in RA.

Il-17A was found to be elevated in RA patients. Although the increase in IL-17A was modest (approximately 3-fold) it was highly statistically significant. This is the first time that Il-17A has been shown to be elevated in RA patients compared to controls in plasma and furthermore the magnitude of the elevation was modest and at a low concentration (average approx 1 pg/mL).

Similar to Il-17A, heterodimer Il-17A/F was found elevated in RA patients. This is the first time that the concentrations of this heterodimer have been shown in blood serum from healthy volunteers, or serum from RA patients or matched controls.

IL-6 was found elevated in RA patients versus controls. It has been previously shown that IL-6 is elevated in RA patients; however, it has never been shown that IL-6 elevation correlates with elevations of Il-7A, IL-17F, IL-17A/F, and/or cTnI in some subjects and does not correlate with such elevations in other subjects.

IL-1β was shown to be decreased in RA patients. This is the first time that this serum biomarker has been shown to be down-regulated in RA.

The measurement of differences in the biomarker concentrations, either up- or down-regulated, singly or in combination, in RA patients versus control subjects provides opportunities for better (e.g., simpler, earlier, faster) disease diagnosis, disease staging, risk classification, disease progression, disease severity and/or identification of therapy responders/non-responders.

TABLE 1

Comparison of biomarker concentrations in healthy volunteer (HV) blood donors and subjects with rheumatoid arthritis.

| Biomarker | Unit | Healthy Mean ± SD | Healthy Range | RA Mean ± SD | RA Range | p-Value | Sample Volume (ul) |
|---|---|---|---|---|---|---|---|
| CRP | ng/mL | 3.5 ± 3.0 | 0.8-8.8 | 11.4 ± 16.0 | 0.4-49.3 | 0.4188 | 0.0005 |
| TNF RI | ng/mL | 2.4 ± 0.6 | 1.4-3.7 | 2.5 ± 0.8 | 1.5-3.9 | 0.9142 | 0.1 |
| TNF RII | ng/mL | 6.2 ± 1.8 | 3.6-9.8 | 7.3 ± 2.5 | 3.7-13.1 | 0.2811 | 0.01 |
| totMMP-9 | ng/mL | 5.1 ± 1.9 | 2.4-8.6 | 2.8 ± 1.6 | 0.9-7.1 | 0.0043 | 0.001 |
| proMMP-9 | ng/mL | 1.0 ± 0.3 | 0.5-1.5 | 0.6 ± 0.4 | 0.2-1.3 | 0.0461 | 0.05 |
| IL-1 RA | ng/mL | 1.2 ± 0.4 | 0.7-2.0 | 0.8 ± 0.5 | 0.2-1.7 | 0.0753 | 10 |
| TIMP-2 | pg/mL | 156 ± 16 | 140-192 | 156 ± 30 | 91-204 | 0.6273 | 0.01 |
| MMP-2/TIMP2 | pg/mL | 76 ± 12 | 61-95 | 79 ± 15 | 43-105 | 0.4182 | 0.1 |
| IL-17F | pg/mL | 41 ± 32 | 16-116 | 579 ± 1002 | 63-3937 | 0.0002 | 10 |
| TNFα | pg/mL | 7.9 ± 1.6 | 5.9-11.0 | 16.4 ± 31.5 | 5.0-129.9 | 0.905 | 10 |
| cTnI | pg/mL | 2.3 ± 1.0 | 1.3-4.5 | 11.5 ± 23.1 | 1.3-95.9 | 0.1042 | 20 |
| IL-6 | pg/mL | 1.7 ± 1.7 | 0.6-5.9 | 3.1 ± 2.3 | 0.7-7.0 | 0.0423 | 5 |
| IL-1β | pg/mL | 2.2 ± 1.0 | 1.1-3.9 | 0.44 ± 0.18 | 0.25-0.90 | 0.0003 | 40 |
| IL-17A | pg/mL | 0.13 ± 0.03 | 0.07-0.18 | 0.36 ± 0.28 | 0.11-1.30 | 0.0033 | 100 |
| IL-17A/F | pg/mL | 0.73 ± 0.35 | 0.37-1.35 | 1.81 ± 1.73 | 0.56-7.14 | 0.0033 | 100 |

Note:
one RA pt was excluded from the IL-1β calculations due to the 99.99% probability of the value being an outlier (>4 SD from the mean; 30.11 pg/ml)

TABLE 2

Comparison of biomarker concentrations in healthy volunteer (HV) blood donors and subjects with rheumatoid arthritis (median values).

| Biomarker | Unit | Healthy Median | RA Median |
|---|---|---|---|
| CRP | ng/mL | 2.62 | 3.79 |
| TNF RI | ng/mL | 2.34 | 2.35 |
| TNF RII | ng/mL | 6.23 | 7.05 |
| totMMP-9 | ng/mL | 5.01 | 2.65 |
| proMMP-9 | ng/mL | 0.96 | 0.68 |
| IL-1 RA | ng/mL | 1.25 | 0.55 |
| TIMP-2 | pg/mL | 148 | 148 |
| MMP-2/TIMP2 | pg/mL | 72 | 78 |
| IL-17F | pg/mL | 30.4 | 190 |
| TNFα | pg/mL | 7.5 | 7.6 |
| cTnI | pg/mL | 2.1 | 4.1 |
| IL-6 | pg/mL | 1.0 | 2.0 |
| IL-1β | pg/mL | 2.26 | 0.44 |
| IL-17A | pg/mL | 0.14 | 0.32 |
| IL-17A/F | pg/mL | 0.62 | 1.15 |

TABLE 3

Percent or fold change in plasma biomarker concentration for RA patients versus HV

| Biomarker | Healthy Mean ± SD | Healthy Range | RA Mean ± SD | RA Range | p-Value | Mean change HV to RA | % or fold change HV to RA |
|---|---|---|---|---|---|---|---|
| totMMP-9 | 5.1 ± 1.9 | 2.4-8.6 | 2.8 ± 1.6 | 0.9-7.1 | 0.0043 | −2.3 | −45% |
| proMMP-9 | 1.0 ± 0.3 | 0.5-1.5 | 0.6 ± 0.4 | 0.2-1.3 | 0.0461 | −0.4 | −40% |
| IL-17F | 41 ± 32 | 16-116 | 579 ± 1002 | 63-3937 | 0.0002 | +538 | +14-fold |
| cTnI | 2.3 ± 1.0 | 1.3-4.5 | 11.5 ± 23.1 | 1.3-95.9 | 0.1042 | +9.2 | +4-fold |
| IL-6 | 1.7 ± 1.7 | 0.6-5.9 | 3.1 ± 2.3 | 0.7-7.0 | 0.0423 | +1.4 | +82% |
| IL-1β | 2.2 ± 1.0 | 1.1-3.9 | 0.44 ± 0.18 | 0.25-0.90 | 0.0003 | −1.76 | −80% |
| IL-17A | 0.13 ± 0.03 | 0.07-0.18 | 0.36 ± 0.28 | 0.11-1.30 | 0.0033 | +0.23 | +2.8-fold |
| IL-17A/F | 0.73 ± 0.35 | 0.37-1.35 | 1.81 ± 1.73 | 0.56-7.14 | 0.0033 | +1.08 | +2.5-fold |

Note:
one RA pt was excluded from the IL-1β calculations due to the 99.99% probability of the value being an outlier (>4 SD from the mean; 30.11 pg/ml)

TABLE 4

Raw biomarker concentration data, in pg/ml.

| ID# | cTnI | IL-1b | IL-1 RA | TNF RI | TNF RII | TNFa | IL-6 | IL-17F | IL-17A |
|---|---|---|---|---|---|---|---|---|---|
| HV1 |  | 1.26 | 709 | 1339 | 3624 | 8.1 | 1 | 31.2 | 0.14 |
| HV2 | 4.5 | 3.87 | 1303 | 2126 | 4650 | 6.3 | 0.6 | 30.4 | 0.13 |
| HV3 | 2.2 | 2.36 | 1512 | 2762 | 6742 | 8.5 | 1.7 | 26.8 | 0.14 |
| HV4 | 2.7 | 1.34 | 756 | 1970 | 5210 | 6.8 | 1.1 | 71.2 | 0.15 |
| HV5 | 1.7 | 3.67 | 2016 | 3727 | 9784 | 11 | 2.4 | 16 | 0.18 |
| HV6 | 2.9 | 1.84 | 1253 | 2336 | 5445 | 5.9 | 0.7 | 20.1 | 0.07 |
| HV7 | 1.6 | 1.06 | 758 | 2192 | 6443 | 7.5 | 0.8 | 33.3 | 0.16 |
| HV8 | 1.3 | 2.54 | 1362 | 2485 | 6232 | 7.5 | 5.9 | 115.8 | 0.09 |
| HV9 | 1.9 | 2.26 | 796 | 2426 | 7397 | 9.8 | 1.1 | 21.2 | 0.13 |
| RA1 | 3 | 0.54 | 986 | 2351 | 5414 | 6.7 | 6.8 | 616.7 | 0.11 |
| RA2 | 3.6 | 0.9 | 478 | 2998 | 7077 | 7.2 | 3.2 | 62.7 | 0.55 |
| RA3 | 14.3 | 0.44 | 545 | 2583 | 7347 | 5.6 | 6.5 | 1417.3 | 0.51 |
| RA4 | 5.9 | 0.38 | 748 | 2603 | 7638 | 10.6 | 2.7 | 139 | 0.18 |
| RA5 | 1.3 | 0.35 | 341 | 1629 | 5211 | 7.6 | 2.2 | 121.5 | 0.42 |
| RA6 | 1.6 | 0.54 | 1504 | 2368 | 7367 | 10.8 | 5.9 | 191.1 | 0.11 |
| RA7 |  | 0.25 | 432 | 2273 | 6345 | 9.5 | 1.7 | 92.4 | 0.38 |
| RA8 | 13.7 | 0.7 | 515 | 1815 | 5368 | 6.4 | 1.1 | 75.5 | 0.26 |

TABLE 4-continued

Raw biomarker concentration data, in pg/ml.

| ID# | cTnI | IL-1b | IL-1 RA | TNF RI | TNF RII | TNFa | IL-6 | IL-17F | IL-17A |
|---|---|---|---|---|---|---|---|---|---|
| RA9  | 1.3  | 0.33  | 286  | 1870 | 5377  | 6.2   | 1.3 | 190.1  | 0.32 |
| RA10 | 1.5  | 0.28  | 244  | 3853 | 10460 | 15.1  | 1   | 85.1   | 0.37 |
| RA11 | 95.9 | 30.11 | 1717 | 3689 | 13119 | 129.9 | 7   | 3936.6 | 1.3  |
| RA12 | 18.6 | 0.33  | 481  | 1549 | 3727  | 7.6   | 0.7 | 329.5  | 0.2  |
| RA13 | 3.1  | 0.45  | 1533 | 1832 | 5464  | 7.4   | 2   | 883.2  | 0.12 |
| RA14 | 4.5  | 0.73  | 842  | 1987 | 5612  | 5     | 1.2 | 143.3  | 0.51 |
| RA15 | 1.8  | 0.33  | 890  | 3638 | 11348 | 10.4  | 3.3 | 395.2  | 0.37 |
| RA16 | 4.6  | 0.38  | 382  | 3910 | 9643  |       |     |        | 0.26 |
| RA17 | 8.6  | 0.62  | 1410 | 1984 | 7047  |       |     |        | 0.19 |

TABLE 5

Raw biomarker concentration data, in pg/ml, continued.

| ID# | MMP2/TIMP2 | MMP-2 | totMMP9 | proMMP9 | CRP | IL-17AF | RF |
|---|---|---|---|---|---|---|---|
| HV1  | 73  | 54 | 5239 | 955  | 7038  | 0.37 | 0 |
| HV2  | 91  | 56 | 6994 | 1262 | 903   | 0.62 | 0 |
| HV3  | 67  | 54 | 3200 | 582  | 4481  | 0.55 | 0 |
| HV4  | 72  | 54 | 4236 | 776  | 2624  | 0.52 | 0 |
| HV5  | 61  | 50 | 5006 | 942  | 8790  | 1.29 | 0 |
| HV6  | 70  | 49 | 5517 | 1240 | 886   | 0.69 | 0 |
| HV7  | 95  | 69 | 2377 | 508  | 770   | 0.67 | 0 |
| HV8  | 85  | 58 | 8556 | 1493 | 1059  | 0.49 | 0 |
| HV9  | 71  | 53 | 4843 | 1169 | 5291  | 1.35 | 0 |
| RA1  | 67  | 46 | 7126 | 1154 | 8846  | 0.56 | 100 |
| RA2  | 73  | 49 | 4691 | 995  | 19660 | 1.57 | 100 |
| RA3  | 43  | 28 | 3347 | 1340 | 33972 | 1.55 | 100 |
| RA4  | 78  | 56 | 2724 | 458  | 2483  | 1.13 | 100 |
| RA5  | 75  | 53 | 4144 | 797  | 6812  | 0.71 | 86.2 |
| RA6  | 66  | 53 | 3536 | 860  | 49340 | 0.9  | 68.9 |
| RA7  | 71  | 53 | 1226 | 209  | 383   | 1.12 | 42.8 |
| RA8  | 78  | 61 | 2329 | 663  | 4136  | 0.75 | 71 |
| RA9  | 103 | 79 | 1212 | 157  | 1360  | 1.73 | 92.4 |
| RA10 | 77  | 74 | 900  | 151  | 667   | 0.69 | 59 |
| RA11 | 105 | 85 | 2690 | 656  | 44292 | 7.14 | 100 |
| RA12 | 79  | 61 | 2608 | 742  | 1395  | 1.15 | 44.7 |
| RA13 | 78  | 61 | 1251 | 277  | 3792  | 5.06 | 82.1 |
| RA14 | 87  | 75 | 3986 | 993  | 1054  | 1.91 | 43.2 |
| RA15 | 70  | 49 | 2652 | 733  | 14137 | 1.49 | 63.9 |
| RA16 | 102 | 83 | 1467 | 173  | 944   | 0.91 | 28.69 |
| RA17 | 92  | 74 | 1828 | 681  | 1014  | 2.39 | 100 |

Table 6 shows AuROC as a measure of predictive power for RA. AuROC does not depend on specifying a cut-point and can be interpreted as the probability that a random RA patient will be classified correctly. AuROC >0.8 suggests very good performance. Odds ratios require specification of a somewhat arbitrary cut-point, wherein the large CIs show the uncertainty in the odds ratios caused by small sample size.

TABLE 6

AuROC analysis of RA biomarkers

| Marker | AuROC | p-Value | Odds Ratio (95% CI) |
|---|---|---|---|
| IL-17F     | 0.941 | 0.0001 | 56 (3.3, 2700) |
| IL-17A     | 0.863 | 0.0018 | 16 (1.7, 208) |
| IL-17 A/F  | 0.863 | 0.0018 | 56 (3.3, 2700) |
| Total MMP-9 | 0.85 | 0.0029 | 0.088 (0.0072, 0.79) |
| IL-6       | 0.735 | 0.051  | 5 (0.63, 60) |
| TNFa       | 0.569 | 0.5967 | 3.1 (0.40, 38) |

Although various specific embodiments of the present invention have been described herein, it is to be understood that the invention is not limited to those precise embodiments and that various changes or modifications can be affected therein by one skilled in the art without departing from the scope and spirit of the invention.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in molecular biology, immunology, chemistry, biochemistry or in the relevant fields are intended to be within the scope of the appended claims.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Particular methods, devices, and materials are described, although any methods and materials similar or equivalent to those described herein can be used in the practice or testing of the invention. The disclosures of all references and publications cited herein are expressly incorporated by reference in their entireties to the same extent as if each were incorporated by reference individually.

We claim:

1. A method for predicting the risk for developing rheumatoid arthritis in a subject, comprising:
   (a) obtaining a blood, serum, or plasma sample from the subject;
   (b) determining a concentration of each of interleukin 17A (IL-17A), interleukin 17A/F (IL-17A/F), and interleukin 17F (IL-17F), wherein the concentration of at least one of the IL-17A, IL-17A/F, and IL-17F is determined in an assay comprising (i) contacting the sample with a label comprising a binding partner for the at least one of IL-17A, IL-17A/F, and IL-17F and a detectable moiety, (ii) counting individual digital events representing binding of the binding partner to the at least one of the IL-17A, IL-17A/F, and IL-17F, wherein each individual digital event comprises a signal representing a single molecule of the at least one of the IL-17A, IL-17A/F, and IL-17F in the sample, (iii) determining a total signal as a sum of the individual digital events, and (iv) relating the sum to the concentration of the at least one of IL-17A, 17A/F, and IL-17F in the sample,
   (c) comparing the levels of IL-17A, IL-17A/F, and IL-17F to threshold concentrations of 0.18 pg/mL for IL-17A, 1.35 pg/mL for IL-17A/F, and 116 pg/mL for IL-17F, and
   (d) predicting that the subject has a greater than normal risk of developing rheumatoid arthritis when the concentrations of IL-17A, IL-17A/F, and IL-17F in the sample are each greater than the threshold concentrations.

2. The method of claim 1, wherein when the subject has a concentration of IL-17A greater than 0.18 pg/ml, of IL-17A/F greater than 1.35 pg/ml and of IL-17F of greater than 116 pg/ml, the subject is predicted to have a greater than normal risk of developing rheumatoid arthritis.

3. The method of claim 1, wherein when the subject has a concentration of IL-17A greater than 0.18 pg/ml, of IL-17A/F greater than 1.35 pg/ml, or of IL-17F of greater than 116 pg/ml, in combination with one or more of a concentration of interleukin IL-1β (IL-1β), less than healthy volunteer average concentrations for IL-1β, a concentration of interleukin 6 (IL-6) greater than healthy volunteer average concentrations for IL-6, or a concentration of total precursor and active matrix metallopeptidase 9 (totMMP-9) less than healthy volunteer average concentrations for totMMP-9, the subject is predicted to have a greater than normal risk of developing rheumatoid arthritis.

4. The method of claim 1, wherein when the subject has a concentration of IL-17A greater than 0.18 pg/ml, of IL-17A/F greater than 1.35 pg/ml and of IL-17F of greater than 116 pg/ml, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject is predicted to have a greater than normal risk of developing rheumatoid arthritis.

5. The method of claim 1, wherein when the subject has a concentration of IL-17A greater than 0.18 pg/ml, of IL-17A/F greater than 1.35 pg/ml or of IL-17F of greater than 116 pg/ml, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject is predicted to have a greater than normal risk of developing rheumatoid arthritis.

6. The method of claim 1, wherein when the subject has a concentration of IL-17A greater than 0.18 pg/ml, of IL-17A/F greater than 1.35 pg/ml, and of IL-17F of greater than 116 pg/ml, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject is predicted to have a greater than normal risk of developing rheumatoid arthritis.

7. The method of claim 1, wherein the binding partner is an antibody.

8. The method of claim 1, further comprising determining a concentration of one or more of IL-1β, IL-6, totMMP-9, precursor protein of matrix metallopeptidase 9 (proMMP-9), and cardiac troponin I (cTnI) in the sample.

9. A method for predicting the risk for developing rheumatoid arthritis in a subject, comprising:
   (a) determining healthy volunteer average concentrations in blood for IL-17A, IL-17A/F, and IL-17F,
   (b) obtaining a blood, serum,. or plasma sample from the subject;
   (c) determining a blood concentration of each of IL-17A, IL-17A/F, and IL-17F, wherein the concentration of at least one of the IL-17A, IL-17A/F, and IL-17F is determined in an assay comprising (i) contacting the sample with a label comprising a binding partner for the at least one of IL-17A, IL-17A/F, and IL-17F and a detectable moiety, (ii) counting individual digital events representing binding of the binding partner to the at least one of the IL-17A, IL-17A/F, and IL-17F, wherein each individual digital event comprises a signal representing a single molecule of the at least one of the IL-17A, IL-17A/F, and IL-17F in the sample, (iii) determining a total signal as a sum of the individual digital events, and (iv) relating the sum to the concentration of the at least one of IL-17A, IL-17A/F, and IL-17F in the sample, and (d) predicting that the subject has a greater than normal risk of developing rheumatoid arthritis when the subject has a concentration of IL-17A, IL-17A/F, and IL-17F greater than healthy volunteer average concentrations for IL-17A, IL-17A/F, and IL-17F.

10. The method of claim 9, wherein when the subject has a concentration of IL-17A, IL-17A/F, or IL-17F greater than healthy volunteer average concentrations for IL-17A, IL-17A/F, or IL-17F, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject is predicted to have a greater than normal risk of developing rheumatoid arthritis.

11. The method of claim 9, wherein when the subject has a concentration of IL-17A, IL-17A/F, or IL-17F greater than healthy volunteer average concentrations for IL-17A, IL-17A/F, or IL-17F, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject is predicted to have a greater than normal risk of developing rheumatoid arthritis.

12. The method of claim 9, wherein when the subject has a concentration of IL-17A, IL-17A/F, and IL-17F greater than healthy volunteer average concentrations for IL-17A, IL-17A/F, and IL-17F, in combination with one or more of a concentration of IL-1β less than healthy volunteer average concentrations for IL-1β, a concentration of IL-6 greater than healthy volunteer average concentrations for IL-6, or a concentration of totMMP-9 less than healthy volunteer average concentrations for totMMP-9, the subject is predicted to have a greater than normal risk of developing rheumatoid arthritis.

13. The method of claim 9, wherein when the subject has a concentration of IL-17A, IL-17A/F, and IL-17F greater than healthy volunteer average concentrations for IL-17A, IL-17A/F, and IL-17F, in combination with a concentration of IL-1β less than healthy volunteer average concentrations for IL-1β, a concentration of IL-6 greater than healthy volunteer average concentrations for IL-6, and a concentration of totMMP-9 less than healthy volunteer average concentrations for totMMP-9, the subject is predicted to have a greater than normal risk of developing rheumatoid arthritis.

14. The method of claim 9, wherein when the subject has a concentration of IL-17A greater than 0.18 pg/ml, of IL-17A/F greater than 1.35 pg/ml, or of IL-17F of greater than 116 pg/ml, in combination with one or more of a concentration of IL-1β less than 1.1 pg/ml, a concentration of IL-6 greater than 1.0 pg/ml, or a concentration of totMMP-9 less than 5.0 ng/ml, the subject is predicted to have a greater than normal risk of developing rheumatoid arthritis.

15. The method of claim 9, wherein when the subject has a concentration of IL-17A greater than 0.18 pg/ml, of IL-17A/F greater than 1.35 pg/ml, and of IL-17F of greater than 116 pg/ml, in combination with one or more of a concentration of IL-1β less than 1.1 pg/ml, a concentration of IL-6 greater than 1.0 pg/ml, or a concentration of totMMP-9 less than 5.0 ng/ml, the subject is predicted to have a greater than normal risk of developing rheumatoid arthritis.

16. The method of claim 9, wherein when the subject has a concentration of IL-17A greater than 0.18 pg/ml, of IL-17A/F greater than 1.35 pg/ml, or of IL-17F of greater than 116 pg/ml, in combination with a concentration of IL-1β less than 1.1 pg/ml, a concentration of IL-6 greater than 1.0 pg/ml, and a concentration of totMMP-9 less than 5.0 ng/ml, the subject is predicted to have a greater than normal risk of developing rheumatoid arthritis.

17. The method of claim 9, wherein when the subject has a concentration of IL-17A greater than 0.18 pg/ml, of IL-17A/F greater than 1.35 pg/ml, and of IL-17F of greater than 116 pg/ml, in combination with a concentration of IL-1β less than 1.1 pg/ml, a concentration of IL-6 greater than 1.0 pg/ml, and a concentration of totMMP-9 less than 5.0 ng/ml, the subject is predicted to have a greater than normal risk of developing rheumatoid arthritis.

18. The method of claim 9, wherein when the subject has a concentration of IL-17A, IL-17A/F, or IL-17F greater than healthy volunteer average concentrations for IL-17A, IL-17A/F, or IL-17F, in combination with one or more of a concentration of IL-1β less than 1.1 pg/ml, a concentration of IL-6 greater than 1.0 pg/ml, or a concentration of totMMP-9 less than 5.0 ng/ml, the subject is predicted to have a greater than normal risk of developing rheumatoid arthritis.

19. The method of claim 9, wherein when the subject has a concentration of IL-17A, IL-17A/F, or IL-17F greater than healthy volunteer average concentrations for IL-17A, IL-17A/F, or IL-17F, in combination with a concentration of IL-1β less than 1.1 pg/ml, a concentration of IL-6 greater than 1.0 pg/ml, and a concentration of totMMP-9 less than 5.0 ng/ml, the subject is predicted to have a greater than normal risk of developing rheumatoid arthritis.

20. The method of claim 9, wherein when the subject has a concentration of IL-17A, IL-17A/F, and IL-17F greater than healthy volunteer average concentrations for IL-17A, IL-17A/F, and IL-17F, in combination with one or more of a concentration of IL-1β less than 1.1 pg/ml, a concentration of IL-6 greater than 1.0 pg/ml, or a concentration of totMMP-9 less than 5.0 ng/ml, the subject is predicted to have a greater than normal risk of developing rheumatoid arthritis.

21. The method of claim 9, wherein when the subject has a concentration of IL-17A, IL-17A/F, and IL-17F greater than healthy volunteer average concentrations for IL-17A, IL-17A/F, and IL-17F, in combination with a concentration of IL-1β less than 1.1 pg/ml, a concentration of IL-6 greater than 1.0 pg/ml, and a concentration of totMMP-9 less than 5.0 ng/ml, the subject is predicted to have a greater than normal risk of developing rheumatoid arthritis.

22. The method of claim 9, wherein the binding partner is an antibody.

23. The method of claim 9, further comprising determining a concentration of one or more of IL-1β, IL-6, totMMP 9, proMMP-9, and cTnI in the sample.

* * * * *